United States Patent [19]
Crossley et al.

[11] Patent Number: 5,753,676
[45] Date of Patent: May 19, 1998

[54] 6-ARYL-(METHYL - OR METHYLIDONE)-QUINOLINE DERIVATIVES AS VOLTAGE-GATED POTASSIUM CHANNEL BLOCKERS

[76] Inventors: Roger Crossley, 21 Silver Fox Crescent, Woodley, Reading, Berkshire SL6 3JA, England; Albert Opalko, 9 Norden Meadows, Maidenhead Berkshire SL6 4SB, England; Peter Jonathan Meade, 53 Moor Lane, Maidenhead Berkshire SL6 7JX, England; Anderson Decourtney Ifill, 63 Campion Hall Drive, Didcot Oxfordshire OX11 9RL, England; Brian John Bushell, 2 Norton Drive Fareham, Hampshire PO16 7PY, England

[21] Appl. No.: 448,467
[22] PCT Filed: Feb. 10, 1995
[86] PCT No.: PCT/GB95/00277
§ 371 Date: Sep. 29, 1995
§ 102(e) Date: Sep. 29, 1995
[87] PCT Pub. No.: WO95/21825
PCT Pub. Date: Aug. 17, 1995

[30] Foreign Application Priority Data

Feb. 10, 1994 [GB] United Kingdom ............... 9402561
Dec. 15, 1994 [GB] United Kingdom ............... 9425345

[51] Int. Cl.$^6$ .................. C07D 215/18; C07D 215/54; A61K 31/47
[52] U.S. Cl. .......... 514/311; 546/152; 546/153; 546/180; 546/181
[58] Field of Search ............... 546/153, 152, 546/181, 180; 514/311

[56] References Cited

U.S. PATENT DOCUMENTS

| | | | |
|---|---|---|---|
| 4,576,949 | 3/1986 | Smith | 514/277 |
| 5,059,609 | 10/1991 | Eggler | 514/314 |
| 5,110,815 | 5/1992 | Effland | 514/228.2 |

FOREIGN PATENT DOCUMENTS

| | | |
|---|---|---|
| 0313295 | 4/1989 | European Pat. Off. |
| 1432378 | 4/1976 | United Kingdom . |
| 1463666 | 2/1977 | United Kingdom . |

OTHER PUBLICATIONS

Chemical Abstracts vol. 83 No. 193044, abstract of Arch. Pharm. (Weinheim, Ger.), 1975, vol. 308(8) pp. 588–594, Albrecht 1975.

Zimmerman and Zeng, J. Org. Chem. 55(16), 4789–91 (1990).

Bennett and Minor, J. Het. Chem. 16(4), 633–35 (1990).

Albrecht and Shröder, Arch. Pharm (Weinheim) 308(8), 588–94 (1975).

Zymalkowski and Kothari, Arch.Pharm (Weinheim) 303(8), 667–75 (1970).

Reimann and Friesinger, Arch Pharm. (Weinheim), 318, 1105–1115 (1985).

*Primary Examiner*—C. Warren Ivy
*Assistant Examiner*—D. Margaret M. Mach
*Attorney, Agent, or Firm*—R. F. Boswell, Jr.

[57] ABSTRACT

This invention concerns a compound of generic formula:

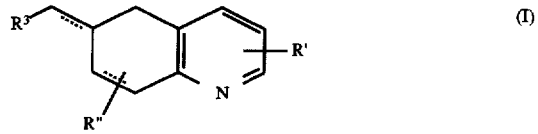

(I)

or a pharmaceutically acceptable salt thereof, where the dotted lines represent optional bonds.

$R^3$ is an optionally substituted $C_6$–$C_{10}$ aryl or heteroaryl group; optionally substituted by one or more substituents the same or different.

R' represents one or more optional substituents the same or different, selected from the following: halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxylamino, optionally substituted $C_6$–$C_{10}$ or heteroaryl or an optionally substituted ($C_6$–$C_{10}$ aryl)alkyl or a heteroaryl alkyl radical; and R" represents one or more optional mono- or di- valent substituents in the 5, 7 or 8 positions the same or different; monovalent substituents being selected from the following: $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxalkyl, $C_7$–$C_{17}$ aralkyloxyamino. R" can also represent hydroxy in the 6 position (when the optional bond is absent); the di-valent substituents being selected from oxo (i.e =O) and methylene (i.e =$CH_2$);

and the N-oxides thereof, which compounds have pharmaceutical uses conferred by their ability to block voltage gated potassium channels.

20 Claims, No Drawings

6-ARYL-(METHYL - OR METHYLIDONE)-QUINOLINE DERIVATIVES AS VOLTAGE-GATED POTASSIUM CHANNEL BLOCKERS

This application is a 371 of PCT/6895/00277, filed Feb. 10, 1995.

This invention relates to nitrogen heterocycles, more particularly to substituted quinolines, to processes for preparing them and to pharmaceutical compositions containing them. The compounds have pharmaceutical uses conferred by their ability to block voltage gated potassium channels.

Voltage gated potassium ion ($K^+$) channels which produce transient outward currents (TOC) are present in the cell membranes of neurones and serve to repolarise the cell following a depolarisation by opening and allowing potassium ions to flow from the inside of the cell to the outside. They are, therefore, one of the main regulating influences on the nerve cell firing and determine the amount of current reaching the terminal regions of the cells. This in turn regulates the amount of neurotransmitter substances released from the nerve terminals. In addition, they help to determine the refractory period of the nerve cell and hence the probability of the cell firing again within a certain time. This governs neuronal excitability and also the tendency of a cell to undergo repetitive firing. An ability to modify the functioning of these channels by chemical means is likely to produce therapeutically useful agents. So far the agents which are known to block the TOC channels are toxins such as the snake toxin dendrotoxin, or 4-aminopyridine and its derivatives. Blockade of the TOC channels leads to a change in the pattern of transmitter release and depending upon the pattern and type of neurone affected different therapeutic ends will result. For example TOC blockers which increase dopaminergic transmission in the substantia nigra will be of use in treatment of Parkinson's disease. Likewise, an increase in cholinergic function is of use in Alzheimer's disease and in cognition enhancement. Because of the complicated neural networks in the brain blockade of the TOC may also lead to increase in more than one transmitter substance at a time and this can act synergistically where a disease state is associated with more than one transmitter deficit as is often the case. It is evident, therefore that TOC blockers may be of use in areas of depression, pain, psychoses, cognition, memory and learning, anxiety, Parkinson's disease and Alzheimer's disease. In addition they can be used as a treatment for conditions where there is an impairment of nerve transmission such as multiple sclerosis.

Compounds which act to increase channel function may be termed channel openers and these serve to increase the braking action of the channels on the cells. In this respect they will also reduce the likelihood of the cells to undergo repetitive firing and may be used as anticonvulsants in the treatment of epilepsy. Also, their action to reduce neurotransmitter release means that they may be used as anaesthetics, analgesics, sedatives and anxiolytics.

This invention provides compounds of generic formula (I):

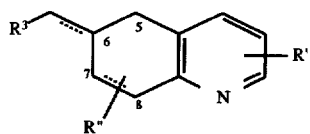

or a pharmaceutically acceptable salt thereof, where the dotted lines represent optional bonds, $R^3$ is an optionally substituted $C_6$–$C_{10}$ aryl or heteroaryl group; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl; $C_1$–$C_6$ alkoxy or such groups substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy) carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$aryl)carbonyl; ($C_2$–$C_7$)alkanoyloxy; ($C_7$–$C_{11}$) aroyloxy; ($C_1$–$C_6$)alkylcarbonylamino, ($C_6$–$C_{10}$aryl) carbonyl amino; ($C_2$–$C_7$) alkoxycarbonylamino; $C_6$–$C_{10}$aryl; heteroaryl as defined above; cyano, $C_1$–$C_6$ aminoalkyl or $C_1$–$C_2$ alkylenedioxy;

R' represents one or more optional substituents the same or different, selected from the following: halogen, $C_1$–$C_6$ alkyl, $C_2$–$C_7$ alkoxycarbonyl, $C_1$–$C_6$ hydroxyalkyl, CN, amninocarbonyl, $C_2$–$C_7$ alkanoyloxy($C_1$–$C_6$)alkyl, carboxy, $C_2$–$C_7$ alkanoxylamino, optionally substituted $C_6$–$C_{10}$ aryl or heteroaryl or an optionally substituted ($C_6$–$C_{10}$ aryl) alkyl or a heteroaryl alkyl radical; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl, $C_1$–$C_6$ alkoxy, or such groups substituted by $C_6$–$C_{10}$ aryl or heteroaryl as defined above; halogen; halo $C_1$–$C_6$ alkyl, halo $C_1$–$C_6$ alkoxy; carboxy; hydroxy($C_1$–$C_6$)alkyl $C_2$–$C_7$ alkanoyloxy($C_1$–$C_6$)alkyl; ($C_1$–$C_6$alkoxy) carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$alkyl)carbonyl; ($C_6$–$C_{10}$ aryl)carbonyl; ($C_2$–$C_7$)alkanoyloxy; ($C_7$–$C_{11}$) aroyloxy; ($C_1$–$C_6$alkyl)carbonylamino, ($C_6$–$C_{10}$aryl) carbonylamino; ($C_2$–$C_7$ alkoxycarbonyl)amino; $C_6$–$C_{10}$ aryl; heteroaryl as defined above; or $C_1$–$C_2$ alkylenedioxy; and R" represents one or more optional mono- or di- valent substituents in the 5, 7 or 8 positions the same or different: monovalent substituents being selected from the following: halogen, $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxalkyl, $C_7$–$C_{17}$ aralkyloxyamino, R' can also represent hydroxy in the 6 position (when the optional bond is absent); the di-valent substituents being selected from oxo (i.e =O) and methylene (i.e =$CH_2$); and the N-oxides thereof.

In a subgeneric aspect this invention provides compounds of formula IA:

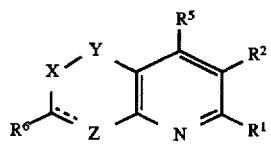

or a pharmaceutically acceptable salt thereof, wherein the dotted line represents an optional bonds with the nitrogen ring optional bonds being between any adjacent ring atoms subject to valency considerations, $R^1$ is H, halogen or a $C_1$–$C_6$ alkyl, optionally substituted $C_6$–$C_{10}$ or heteroaryl or an optionally substituted ($C_6$–$C_{10}$ aryl)alkyl or a heteroarylalkyl radical; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl, $C_1$–$C_6$ alkoxy, or such groups substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g mono- or di-($C_1$–$C_6$ alkyl)-amino; nitro; hydroxy; mercapto; $C_1$–$C6$alkylthio; ($C_1$–$C_6$alkyl)carbonyl; ($C_6$–$C_{10}$ aryl) carbonyl; ($C_2$–$C_7$)alkanoyloxy; ($C_7$–$C_{11}$)aroyloxy; ($C_1$–$C_6$alkyl)carbonylamino, ($C_6$-$C_{10}$aryl)carbonylamino; ($C_2$–$C_7$) alkoxycarbonylamino; $C_6$–$C_{10}$ aryl; heteroaryl as defined above; or $C_1$–$C_2$ alkylenedioxy;

$R^2$ is hydrogen, $C_1$–$C_6$ alkyl, $C_1$–$C_6$ hydroxyalkyl, $C_2$–$C_7$ alkanoyloxy($C_1$–$C_6$)alkyl, $C_2$–$C_7$ alkoxycarbonyl, cyano, aminocarbonyl, carboxy or $C_2$–$C_7$ alkanoylamino;

X is a group of formula

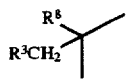 (vii)

or

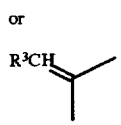 (viii)

where $R^8$ is H or OH;

$R^3$ is a $C_6$–$C_{10}$ aryl or a heteroaryl radical containing 5 to 10 ring atoms of which one or more (e.g up to 3) of said atoms are heteroatoms selected from oxygen, nitrogen and sulphur, the same or different; said aryl or heteroaryl radical being optionally substituted by one or more substituents the same or different as defined above in the definition of R $^1$;

Y is

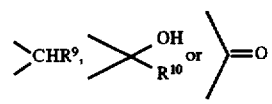

where $R^9$ represents hydrogen, $C_1$–$C_6$ alkyl, C2–$C_7$ alkanoyloxy, optionally substituted heteroaryl, optionally substituted $C_6$–$C_{10}$ aryl or $CH_2OH$; and $R^{10}$ represents hydrogen or $C_1$–$C_6$ alkyl; and $R^4$ when present represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are for example as illustrated above in connection with $R^1$;

Z is C=O, C=$CH_2$, —$CHR^7$— or =$C(R^7)$— where $R^7$ is hydrogen, OH, $CH_2OH$, $NH_2$, $C_2$–$C_7$ alkanoyloxy, $C_2$–$C_7$ alkanoylamino $C_1$–$C_6$alkylamino or a $C_1$–$C_6$ alkyl group optionally substituted by a group $R^3$ as defined above;

$R^5$ is hydrogen, $C_1$–C6 alkyl, $C_6$–$C_{10}$ aryl, heteroaryl or a $C_1$–$C_6$alkyl substituted by $C_6$–$C_{10}$ aryl or heteroaryl; said aryl or heteroaryl groups being optionally substituted as defined for $R^1$ above;

$R^6$ is $NH_2$, $C_7$–$C_{17}$ aralkyloxyanino, $C_2$–$C_7$ alkanoylamino or $R^6$ is one of the values listed for $R^5$ above; and the N-oxide salts thereof.

Included in the projected formula covered by formula I (and IA) above are the following (where Z is $CH_2$, and $R^5$ and $R^6$ are hydrogen):

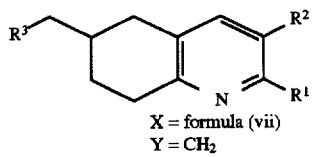

X = formula (vii)
Y = $CH_2$
(Examples 1, 2, 3, 4, 8)

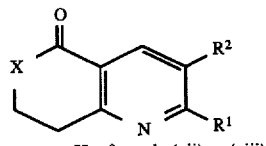

X = formula (vii) or (viii)
Y = CO
(Examples 5, 6, 7)

In all the formulae above, examples of alkyl as a group or part of a group, e.g aralkyl, alkanoyl, are straight or branched chain groups of up to 6 carbon atoms especially of 1 to 4 carbon atoms such as methyl, ethyl, n-propyl, isopropyl, n-butyl and sec butyl. Examples of "alkoxy" as a group or part of a group, e.g alkoxycarbonyl, are groups of formula alkyl-O- where alkyl has the meanings immediately above. Examples of aryl as a group or part of a group, e.g aralkyl, aralkanoyl, are mono- or bicyclic groups of 6 to 10 carbon atoms such as phenyl and naphthyl, e.g 1 or 2-naphthyl. Heteroaryl groups have heteroatoms selected from oxygen, nitrogen and/or sulphur. Examples of heteroaryl as a group or part of a group, e.g heteroarylalkyl, are mono- or bicyclic groups of 5 to 10 ring atoms such as those having one nitrogen heteroatom e.g 2 or 3-pyrrolyl, 2, 3 or 4-pyridyl, quinolyl (e.g 2, 3 or 6-quinolyl) isoquinolyl (e.g 1-, 3- or 6-isoquinolyl); one sulphur atom, e.g 2- or 3-thienyl or benzothienyl (e.g 2, 3 or 6-benzothienyl); or one oxygen atom, e.g 2- or 3-furanyl or benzofuranyl (e.g 2-, 3- or 6-benzofuranyl); or two or more heteroatoms e.g thiazolyl (e.g 2-thiazolyl), imidazolyl (e.g 2-imidazolyl); oxazolyl (e.g 2-oxazolyl).

Examples of optional substitutents are alkyl, alkoxy, aryl and heteroaryl as illustrated above, chlorine, bromine, fluorine, $CF_3$, $CH_2F$, $CF_3CH_2$, $HOCH_2$—, HOCH(Me)—, HO($CH_2$)$_2$—, MeOOC—, EtOOC—, $NH_2$, NHMe—, NHEt—, $NMe_2$—, $NO_2$, HO, HS—, MeS—, EtS—, $CH_3CO$—, EtCO—, PhCO—, $CH_3CONH$—, EtCONH—, PhCONH—, MeOOCNH—, EtOOCNH—, $CH_3CO.O$—, EtCO.O— or methylene- or ethylene-dioxy.

Examples of $R^1$ are hydrogen, methyl, phenyl, benzyl, chlorine and bromine.

The group $R^2$ may be for example hydrogen, methyl, —COOMe, —COOEt or —$CH_2OH$.

$R^3$ may be for example phenyl or phenyl substituted by one or more substitutents as illustrated above, e.g substituents the same or different selected from: $C_1$–$C_6$ alkoxy such as methoxy, ethoxy; halogen such as chlorine or bromine; $CF_3$; $CF_3O$; $C_1$–$C_6$ alkyl such as methyl or ethyl; hydroxy; cyano and carboxy. Preferred values for $R^3$ are methoxyphenyl, e.g 4-methoxyphenyl and hydroxyphenyl, e.g 4-hydroxyphenyl.

Examples of the group Y are $CH_2$, CO, $C=CH_2$, CHOH or $CHOCOCH_3$, (i.e in formula I, R" is absent, $=O$, $=CH_2$, OH or $OCOCH_3$ respectively).

The group Z may be for example $C=O$, $C=CH_2$, $—CH_2—$, $—CH(Me)$; $—CH(Ph)—$, $=CH(Me)$— or $—CH(CH_2Ph)—$, (i.e in formula I, R" represents $=O$, $=CH_2$, absent, Me, Ph, Me or $CH_2Ph$).

Examples of $R^5$ are hydrogen, $C_1$–$C_4$ alkyl, e.g methyl, phenyl, benzyl and substituted phenyl where substituents are as defined hereinabove.

Examples of $R^6$ are hydrogen, $NH_2$ and $NHCOCH_3$.

Preferred compounds of formula I and IA have $R^3$ represents 4-methoxyphenyl. Also preferred are compounds where $R^2$ represents methyl or hydrogen.

Particularly preferred are compounds of formula (H):

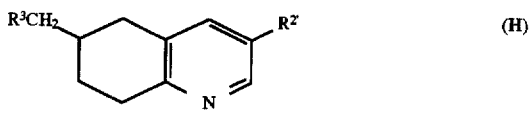

in which formulae $R^{2'}$ is hydrogen, $C_1$–$C_6$ alkyl, $C_2$–$C_7$ alkoxycarbonyl, acetylamino, CN or $CH_2OH$; $R^3$ is as defined above, preferably unsubstituted or substituted phenyl, e.g where the substituents is/are selected from $C_1$–$C_6$ alkyl, $C_1$–$C_6$ alkoxy, hydroxy, halogen and methylene or ethylene-dioxy; and $R^{4'}$ is hydrogen, alkyl or optionally substituted aryl($C_1$–$C_6$) alkyl in which the alkyl group is itself optionally substituted by $C_1$–$C_6$ alkyl.

The compounds of formula I (including subgeneric formulae IA and H, can possess one or more asymmetric centres and accordingly the compounds may exist and be isolated in a number of optically active stereoisomeric forms. When X has formula viii then geometric isomers (E,Z) are also obtained. This invention encompasses the compounds of formula I in any optically active or geometric form or mixtures thereof eg. racemates or diastereoisomers. Standard separation techniques may be used to isolate particular enantiomeric and diastereomeric forms. For example a racemic mixture may be converted to a mixture of optically active diastereoisomers by reaction with a single enantiomer of a 'resolving agent' (for example by diastereomeric salt formation or formation of a covalent bond). The resulting mixture of optically active diastereoisomers may be separated by standard techniques (e.g crystallisation or chromatography) and individual optically active diastereoisomers then treated to remove the 'resolving agent' thereby releasing the single enantiomer of the compound of the invention. Chiral chromatography (using a chiral support, eluent or ion pairing agent) may also be used to separate enantiomeric mixtures directly.

Stereospecific synthesis using optically active starting materials and/or chiral reagent catalyst and/or solvents may also be employed to prepare particular diastereoisomers or even a particular enantiomer.

For example where the compound of formula I is prepared by an addition process creating one or more optical centres then carrying out the reaction using a chiral catalyst or agent or in a chiral environment can give the product as a single enantiomer.

The compounds of formula I possess pharmacological activity in particular they block voltage gated potassium chanels. They may therefore be used to treat CNS disorders as described above such as depression, pain psychoses, anxiety, movement disorders (such as Parkinson's disease) and multiple sclerosis and in enhancing cognition, memory and learning. They demonstrate their ability to block voltage gated potassium channels in dorsal root ganglion cells by the following standard test procedures:

Procedure 1

Modulation of voltage-activated K+ currents in dorsal root ganglion (DRG) cells:

The method used in the culture or dorsal root ganglion cells is similar to that described by Wood et. al., Capsaicin induced ion fluxes in dorsal root ganglion cells in culture, J. Neuroscience, 8, 3208–3220) (1988). Dorsal root ganglia are dissected mainly from around the lumbar and thoracic vertebrae and placed in a conical centrifuge tube containing Ham's F14 nutrient mixture (F14:Imperial Laboratories) plus horse serum (HS: GIBCO or Flow). When all ganglia have been collected (ex ca. 14 pups) the excess medium is removed and the ganglia incubated for 30 min in "F14+HS" containing 0.1% collagenase Type 1A-S (Sigma). Excess medium is removed, ganglia washed in 4 ml F14 (no HS), resuspended and spun down at 900 g for 10 s. The supernatant is again removed and replaced with 1.8 ml F14 (no HS) plus 0.2 ml trypsin (GIBCO) at a final concentration of 0.25%. The ganglia are then incubated at 37° C. for 30 min agitating every 10 min to prevent clumping. The trypsinisation is inhibited by the addition of 6 ml "F14+HS" and cells are resuspended and centrifuged as before. The medium is removed and 2 ml added of "F14+HS" containing 0.4% DNAase 1 (Sigma). The ganglia are then triturated gently 15–20×using a siliconised pasteur pipette, filtered through a 90 mm nylon mesh filter and collected into a centrifuge tube. The filter is further washed with 2 ml of "F14+HS" which is collected into the same tube. The suspension is spun at 900 g for 3 min, the supernatant removed and the cells resuspended in DRG Growth Medium (DRG-GM) which consists of: HAMS F14 nutrient mixture (40%, v/v), HS(10%, v/v) C6 conditioned medium (50%, v/v), penicillin/streptomycin (100 U/ml; 100 μg/ml) and NGF (30 μg/ml). Cells are then plated out onto five 60mm poly-L-lysine-coated tissue culture petri dishes (see below).

Replating

After a few days in culture (3–7 days, usually), cells are resuspended from 60 mm dishes using a 0.25% solution of trypsin in F14. An equal volume of DRG-GM is added to inhibit the trypsin, the cells are spun at 900 g for 5 minutes and resuspended in 0.25–0.5 ml of DRG-GM. Neurites are removed by gentle trituration through a 21 g syringe needle (15–20 strokes) and a drop of the cell suspension is then placed on each of 5–6 poly-D-lysine- and laminin-coated 35 mm petri dishes (see below). After 30 minutes incubation at 37° C., each plate is flooded with ca 1.5 ml DRG-GM and after about I hour incubation, cells are ready for electrophysiological recording. This final step is carried out specifically in order to remove neurites which hinder good voltage-clamp of the cells.

Coating of plates:

2 ml of poly-D-lysine (Sigma), reconsitituted in distilled water to 100 μg/ml, are added to each plate and left for 1–2 hours. Plates are then washed with water and left to dry. Laminin (5 μg/ml) is added as a drop to the centre of plates (previously coated with poly-D-Lys), left for 45 min before removal of excess and use of plates.

Electrophysiology:

Recordings are made using an AxoClamp-2A (Axon Instruments Inc) switiching clamp amplifier using patch electrodes (4–8M ohms), made from borosilicate glass capillary tubes (GC15OTF-10, Clark Electromedical) and fire-polished. Electrodes are filled with (in mM): 140 K Gluconate, 2 $MgCl_2$, 1.1 EGTA/KOH, 5 HEPES, 20 sucrose, 2 MgATP, 0.2 GTP; pH set to 7.2 with KOH and osmolarity adjusted with sucrose to 310 mOsm. The electrodes are then and dipped in Sigmacote (Sigma) prior to recording to reduce stray capacitance. The bathing solution in which cells are continually perfused (during recordings) consists of (in mM): 124 NaCl, 2.5 KCl, 4 $MgCl_2$, 5 HEPES, 10 glucose, 1 µM TTX, 20 sucrose pH set to 7·4 with NaOH and osmolarity adjusted with sucrose to 320 mOsm. $Ca^{2+}$ is omitted from the bathing medium in order to minimise voltage-activated $Ca^{2+}$ currents and $Ca^{2+}$ activated K+ currents. TTX is included to block voltage-activated $Na^+$ currents, although in some recordings a residual TTX-resistant $Na^+$ current is evident. Recordings are made in voltage-clamp mode using a voltage-step protocol consisting of:

i) holding potential $(V_h)$=−30 mV (in order to inactivate transient outward current)
ii) 1s prepulse to −100 mV
iii) 1s pulse to +6OmV to activate total outward current
iv) return to −30 mV In some cases current-voltage (I-V) relationships are obtained in the presence and absence of test compound by constructing families of voltage steps over a range of membrane potentials (−100 mV to +60 mV) from a holding potential of either −30 mV or −100 mV. Voltage steps and data acquisition (current responses) are controlled by an Atari MegaSTE computer interfaced to the voltage-clamp via an ITC-16 ADC/DAC (Instrutech Corp.) and subsequent analysis carried out using REVIEW (Instrutech Corp). Test compounds are applied to individual neurones by a local microperfusion system, initially at a test concentration of 100 or 10 µM (solubility-permitting).

Calculations:

Current responses during the test voltage step to +60 mV (above) are measured off-line using REVIEW (Instrutech Corp). The following measurements are made:

peak (with ca.50 ms) and Q integral (t=1s) outward current measured at +60 mV:
  i) after conditioning prepulse to −100 mV (includes non-inactivating as well as transient outward current (TOC)
  ii) without conditioning prepulse (mainly non-inactivating current)
  iii) difference (digital subtraction) of above currents corresponds to TOC).

Current amplitudes are obtained for: total outward current ($K_{-100}$), noninactivating current ($K_{-30}$) and TOC. Peak current amplitudes recorded in the presence of test compounds are expressed as a percentage of the corresponding control values.

Standard Compounds:
 4-aminopyridine (100% block of TOC at 1 mM)
 Toxin I (50% block of TOC at 100 nM)
 (Toxin I is a dendrotoxin homologue.)

The compounds were also tested for blocking transient outward potassium currents (TOC) in the $GH_3$ rat pituitary cell line according to the procedure below:

Procedure 2:

$GH_3$ cells were obtained from either Flow Laboratories or European Centre for Animal Cell Cultures (Porton Down), and maintained in tissue culture using standard procedures and media for this cell line. Cells were plated on 35 mm plastic dishes and used subsequently for electrophysiology within 1 to 10 days. Currents were recorded using the whole-cell voltage clamp configuration of the patch-clamp technique, using an Axopatch 1C amplifier (Axon Instruments). Patch electrodes were manufactured from aluminosilicate glass tubing (Clark Electomedical SM 150F-10) and heat polished prior to use. Resistance was 1–5 MΩ. No electrode coating was necessary for whole-cell recording. Signal acquisition and analysis was performed using pClamp software (Axon Instruments). A p-on4 subtraction procedure was used to remove leak and capacitative currents on line. A holding potential of −100 mV was routinely used: this avoided accumulation of slow voltage-dependent inactivation. Two main protocols were used in testing drugs. 1) Current-voltage (I-V) curves were collected, with incrementing steps of either 10 or 20 mV. Full I-V curves were obtained both in control and drug solutions. 2) a 'pharmacology' program, which involved single voltage steps fromm −100 to +60 mV. applied and collected at 20s intervals. Compounds under investigation were applied via a 'U' tube rapid application system to a small area of the recording chamber. Drug applications were always bracketed by control solutions to ensure reversibility. The recording chamber was continously perfused at 1–5 ml.min$^{-1}$. Results are expressed as % of control peak current (step from −100 to +60 mV). However, where drugs have a time dependent effect on TOC, i.e acceleration of TOC decay, results are also expressed as a % of total charge transferred within a defined period of the voltage step from −100 to +60 mV.

The standard extracellular solution contained (in mM): NaCl 135 (or choline or TRIS chloride); KCl 5; $MgCl_2$ 4; EGTA 1; TEACl 10; HEPES 10; glucose 25; pH set to 7.4 with NaOH. TTX was usually included at 100–200 nM. The intracellular (pipette) solution was comprised of (in mM): K aspartate 120; KCl 20; $MgCl_2$ 1; cAMP 1; MgATP 2; EGTA 10; HEPES 10; pH 7.4 with KOH. Other intracellular substrates were often used without noticeable effect. This solution was stored in 1ml aliquots at −4° C., and filtered at 0.2 µm. These recording solutions precluded activation of voltage dependent Na, Ca, delayed rectifier and Ca-activated K currents. The resulting whole-cell currents chiefly comprised the transient outward potassium current, switching on with third power kinetics reaching peak amplitudes of ~1 nA at +60 mV, and a double exponential decay (time constants of ~30 and 160ms at +60 mV). There is no significant change in current amplitude within the normal recording period, which may extend for up to 90 min. One dish of cells usually lasts several hours. The standard compound 4-aminopyridine is a block @ 1–5 mM. (80% block at 5 mM).

Results:

Results for representative compounds of this invention in the two abovementioned tests are shown in the Table below:

| | | % Block of TOC | |
| --- | --- | --- | --- |
| COMPOUND EXAMPLE NO | CONCEN- TRATION | PROCEDURE 1 DRG % | PROCEDURE 2 GH3 % |
| 3 | 100 µM | 35 | 34 |
| 6 | 100 µM | — | 48 |
| 8 | 100 µM | 21 | 53 |
| 9 | 10 µM | 25 | — |
| 10 | 10 µM | 18 | — |

The results show the ability of compounds of this invention to block voltage gated potassium channels indicating pharmaceutical uses as described hereinabove.

This invention also provides processes for preparing the compounds of formula I and IA. Many starting materials used herein can be derived from substituted catechols, reduced to give or form many known cyclohexane- 1, 3- or -1,4- diones appropriately protected to give compounds of the type:

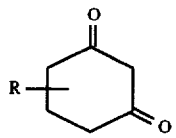

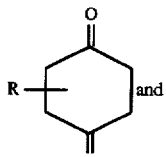 and

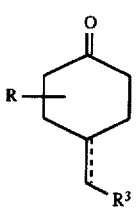

where R is R" or a group convertible thereto, and $R^3$ is as defined herein. Such compounds can be converted to final products or other starting materials as described herein via known pyridine ring syntheses for example:

Comprehensive Organic Chemistry, Vol. 4, Editor P G Sammes, Part 16.1, pages 3–84, Pyridines, by D M Smith, Pergamon Press;

Comprehensive Heterocyclic Chemistry Vol. 2, Editors Boulton and McKillop Part 2A, "Six membered rings with one nitrogen atom", Pergamon Press and The Chemistry of Heterocyclic Compounds. Editor A Weissberger, Pyridine and Its Derivatives, Parts 1–4, (1962), Interscience Publishers.

Compounds of formula I are therefore useful for preparing other compounds of formula I as will be apparent from the processes described herein.

Compounds of formula I may be prepared by one of the following processes where if necessary reactive substituent groups are protected prior to reaction and removed thereafter; said processes comprising:

(A) reacting a compound of formula:

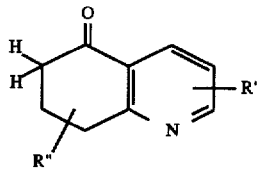 (II)

wherein R' and R" are as defined herein with an aldehyde of formula $R^3CHO$, in the presence of base to give a corresponding compound of formula I which has oxo group in the 5-position and the optional bond to the 6-position is present, or (B) reacting a compound of formula:

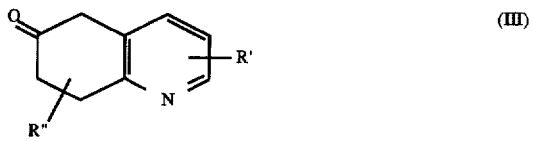 (III)

wherein R' and R" are as defined above with an anion of formula:

$R^3CH_2^{\ominus}$ where $R^3$ is as defined above, e.g using a Grignard reagent, to give a corresponding compound of formula I having a 6-hydroxy group, which compound may be dehydrated to give a compound of formula I wherein the optional bond to the 6-position is present; or (C) reacting a compound of formula (III) as defined above with a Wittig reagent of formula:

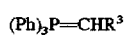

$(Ph)_3P=CHR^3$ wherein $R^3$ is as defined above to give a corresponding compound of formula I where the optional bond to the 6-position is present; or (D) reacting a compound of formula (IV):

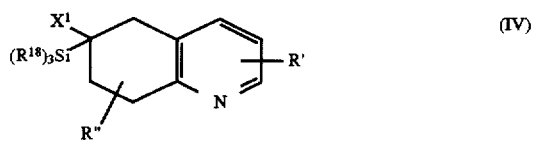 (IV)

wherein R' and R" are as defined above, $(R^{18})_3$ is defined as three $R^{18}$ radicals the same or different selected from alkyl, cycloalkyl, aralkyl, aryl or electron donating substituents such as alkoxy, cycloalkoxy, aralkoxy, aryloxy, alkylthio, cycloalkythio, aralkylthio or arylthio, the group $R^dR^eN$—where $R^d$ and $R^e$ are selected from alkyl, cycloalkyl, aryl and aralkyl or $R^d$ and $R^e$ are joined to form a heterocyclic ring with the nitrogen atom to which they are attached (e.g piperidinyl, pyrrolidinyl which may be substituted, e.g by alkyl) and $X^1$ is sodium, potassium or lithium, with a compound of formula:

$R^3CHO$ wherein $R^3$ is as defined above in connection with formula I; followed by treatment under acidic or basic conditions, to give a compound of formula I in which the optional bond to the 6-position is present; or (E) reacting a compound of formula (III) as defined above with a compound of formula:

 (V)

where $R^3$, $R^{18}$ and $X^1$ are as defined above, followed by treatment under acidic or basic conditions, or (F) converting a compound of formula I having at least one reactive substituent group or siteto give a different compound of formula I; or (G) reducing a compound of formula (L):

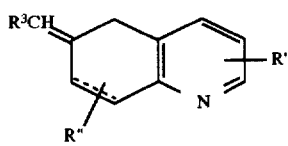

wherein m R', R", $R^3$ and $R^4$ are as defined above e.g catalytically using 5% Pd/C and hydrogen ; to give a compound of formula I wherein the optional bond to the 6-position is absent; or (H) dehydrating a compound of formula (M):

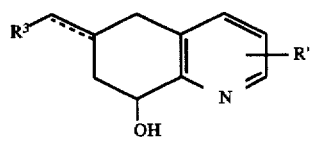

wherein the dotted lines, m, R' and $R^3$ are as defined above, e.g. using polyphosphoric acid and warming, to give a compound of formula I having a double bond between the 7 and 8 positions, or (I) oxidising a compound of formula I using an oxidising agent, e.g a peroxyacid sich as m-chroroxybenzoic acid in an inert solvent, to give an N-oxide of formula I, or (J) converting a basic compound of formula I to an acid addition or quaternary ammonium salt thereof, or vice versa, or (K) resolving a mixture of isomeric compounds of formula I to isolate a specific enantiomeric form substantially in the absence of other isomers.

Processes for preparing the subgeneric aspects of this invention, e.g compounds of formula IA comprise one of the following:

a) cyclising a compound of formula:

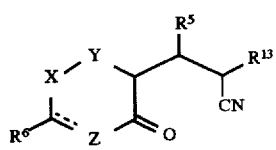

wherein $R^5$, $R^6$, X, Y and Z are as hereinbefore defined and R $^{13}$ is hydrogen, hydroxy($C_1$-$C_6$)alkyl, ($C_2$-$C_7$alkanoyl)oxy($C_1$-$C_6$)alkyl, ($C_1$-$C_6$ alkoxy)carbonyl or $C_1$-$C_6$ alkyl using HBr to give a 5,6,7,8-tetrahydroquinoline of formula IA wherein $R^1$ is bromine and $R^2$ is H, $C_2$-$C_7$alkoxycarbonyl, hydroxy($C_1$-$C_6$)alkyl, ($C_2$-$C_7$alkanoyl)oxy($C_1$-$C_6$)alkyl, or $C_1$-$C_6$ alkyl; or b) reacting a compound of formula (IX):

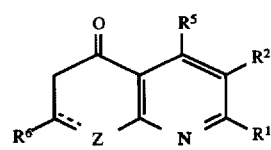

wherein the dotted line, $R^1$, $R^2$, Z, $R^5$ and $R^6$ are as defined above, with an aldehyde of formula $R^3$ CHO, in the presence of base to give a corresponding compound of formula IA wherein X is formula (viii) and Y is C=O; or (c) reacting a compound of formula (X):

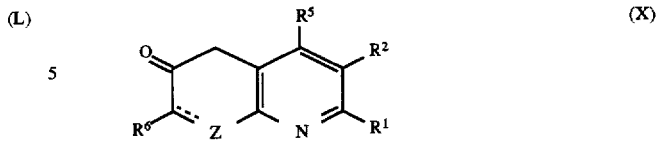

wherein $R^1$, $R^2$, Z, $R^5$, $R^6$ and $R^4$ are as defined above, with an ylide of formula:

(Ph)$_3$P=CHR$^3$ (XI)

wherein $R^3$ is as defined above to give a corresponding compound of formula IA wherein X has formula (viii):

or d) converting any substituent group present in a compound of formula IA to another substituent group by known means; e.g reducing $R^2$ is ($C_1$-$C_6$alkoxy)-carbonyl to give a compound of formula IA wherein $R^2$ is —CH$_2$OH or e) dehalogenating a compound of formula IA wherein $R^2$, X and Y are as defined above, and $R^1$ is halogen, i.e a compound of formula Q:

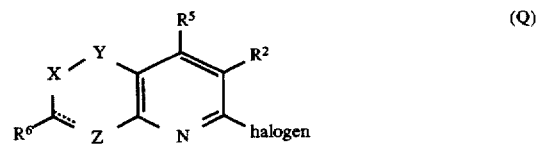

to give a corresponding compound of formula IA wherein $R^1$ is hydrogen; or f) reducing a compound of formula IA wherein Y is

i.e a compound of formula:

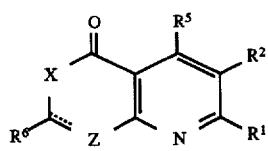

wherein the dotted line R $^1$, $R^2$, $R^4$, $R^5$ and $R^6$ are as defined above, to give a corresponding compound of formula I wherein Y is CH$_2$; or g) reducing a compound of formula IA wherein X has formula (viii) to give a compound of formula IA wherein X has formula (vii) and $R^8$ is hydrogen; or or h) resolving a mixture of isomeric compounds of formula IA using standard separation techniques to isolate a specific enantiomeric form in the absence of other isomers.

Methods for carrying out processes (A)–(K) and (a)–(h) are known in the literature and may be carried out by standard procedures. If required other sites in the molecule can be protected by known methods to avoid side reactions.

With regard to process (a) the cyclisation can be conveniently carried out at room temperature or below using concentrated HBr in acetic acid to give either a hexahydroquinolin-2[1H]-one or a tetrahydroquinoline.

Processes b) and A) are conveniently carried out by heating in the presence of a small amount of organic base, e.g piperidine.

Process B) may be carried out by reacting with a Grignard reagent of formula $R^3CH_2Mghal$ where hal is a halogen such as bromine.

Processes c) and C) may be carried out under Wittig reaction conditions using the desired substituted triphenylphosphonium halide. Processes for carrying out Wittig reactions are extensively described in the literature. See for example Org. React. 14, 270 (1965) and Org. Syn. Coll. Vol. 5 751 (1973).

Process (D) may be carried out under Peterson reaction conditions. In the process an intermediate of formula IV in which XI is $R^3CH(OX)$— (X is Li, Na or K) is formed and this compound is hydrolysed to the alcohol and dehydrated by acid or base treatment, removing any protection groups as required. Process (E) is analogous to Process (D) and may be carried under the same conditions.

With regard to processes (F) and (d) conversions may be carried out by known means, e.g an alcohol may be formed from an ester substituent by reduction using lithium borohydride with heating if desired in the presence of an inert solvent, e.g tetrahydrofuran. Process (d) also includes conversion of substituents on aromatic $R^3$ radicals. Such methods are well known in the art. For example an alkoxy substiuent can be converted to hydroxy using boron tribromide. An arylmethoxy substituent can be hydrogenated to give hydroxy. Nitro substituents can be reduced to amino substituents. Amino substituents can be acylated e.g using an acyl halide to give acylamino, or sulphonylated to give a sulphonamide, or alkylated to give an alkylamino group, e.g by reductive alkylation. Acylated amino groups may be hydrolysed to give an amino substituent.

Process (e) may be carried out using catalytic hydrogenation, e.g using palladium on carbon in an inert solvent if desired in the presence of base, or by chemical reduction.

With regard to process (f) the reaction may be conveniently carried out under conditions suitable for the Wolff-Kishner (Organic Reactions IV p 373 (1948) and Merck Index 7th Edn. 1960 p 1479) to give the compound of formula IA wherein Y is $CH_2$.

Process (g) may be conveniently carried out using a reducing agent e.g a trialkylsilane under acidic conditions such as trifluoroacetic acid. As a by-product hydroxy substitution can also occur to give a compound of formula IA wherein $R^8$ is hydroxy.

As mentioned above standard resolution techniques can be used in process (h) to isolate enantiomeric forms of the compounds of formula I and IA. Such techniques are well known in the art.

Where necessary in the reactions described herein protecting groups may be used to protect reactive sites during a reaction and removed thereafter.

Once a compound of formula I is prepared containing a reactive substituent group or site, e.g an alkanoyloxy substituent,or an acidic proton, then such compounds may be converted to a different compound of formula I e.g hydrolysed to give corresponding hydroxy compounds of formula I. Similarly compounds of formula I containing a hydroxy group may be acylated, e.g using alkanoyl halides to give corresponding alkanoyl compounds of formula I.

Similarly when an alkoxy substituent is present then such compounds may be dealkylated using standard procedures to give corresponding hydroxy compounds of formula I. Accordingly compounds of formula I may also be intermediates for other compounds of formula I.

As discussed above starting materials for the processes described herein are known compounds or can be made by analogous methods for known compounds.

For example compounds of formula (VI) can be prepared by Michael addition to an enamine (formed from a cyclic ketone) as shown in Reaction Scheme I below:

Reaction Scheme I

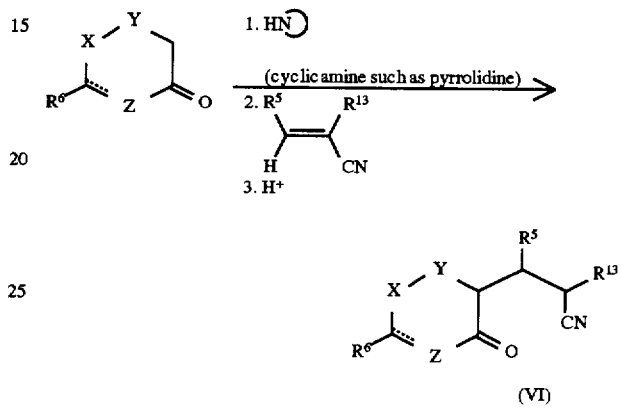

Compounds of formula (IX) may be prepared by one of the following:

i) reacting an appropriately substituted 1,3-cyclohexadione with an appropriate aminoacrolein of formula:

(XIV)

or ii) reacting a compound of formula:

(XV)

with a compound of formula:

(XVI)

wherein Z, $R^2$ and $R^6$ are as defined above, to give a tetrahydroquinoline compound of formula (IX).

Compounds of formula (X) can be prepared by (i) reacting a ketal protected compound of formula

(XIX)

with an aminoacrolein of formula:

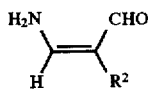

wherein R² is as defined above.

The compounds of this invention may be obtained in free base form or as acid addition salts as desired. Examples of such salts include salts with pharmaceutically acceptable organic or inorganic acids such as hydrochloric, hydrobromic, hydroiodic, sulphuric, phosphoric, nitric, acetic, citric, tartaric, fumaric, succinic, malonic, formic, maleic acid or organosulphonic acids such as methane sulphonic or p-toluene sulphonic acids. N-oxides may be prepared by oxidising compounds of formula I and IA with a peroxyacid, e.g. m-chloroperoxybenzoic acid.

When acidic substituents are present it is also possible to form salts by treatment with bases, to give for example alkali metals (such as sodium) or ammonium salts. Such salts of the compounds of formula I are included within the scope of this invention.

When basic substituents are present then quaternary ammonium salts may be formed by quaternizing with an alkylating agent such as alkyl or aralkyl halides.

This invention also provides pharmaceutical compositions comprising a compound of formula I or a pharmaceutically acceptable salt thereof and a pharmaceutically acceptable carrier. For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or table disintegrating agents; it can also be encapsulating material. In powders the carrier is a finely divided solid which is in admixture with the the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carrier) is surrounded by carriers, which is thus in association with it. Similarly cachets are included. Sterile liquid form compositions include sterile solutions, suspensions, emulsions, syrups and elixirs.The active ingredient can be dissolved or suspended in a pharmaceutically acceptable carrier, such a sterile water, sterile organic solvent or a mixture of both. The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. The composition may be administered orally, nasally, rectally or parenterally. Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 1 to 500 mg or more. e.g 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound and the disease to be treated. For certain of the abovementioned conditions it is clear that the compounds may be used prophylactically as well as for the alleviation of acute symptoms. References herein to "treatment" or the like are to be understood to include such prophylactic treatment, as well as treatment of acute conditions.

The following Examples illustrate the invention and methods for preparing compounds of the invention. In the Examples relative configurations of optical centres are denoted using the R,S notation. As used herein (±)-(3RS, 6SR), means a racemic mixture of the 3R, 6S, and 3S, 6R, enantiomers. Where the optical rotation is known but the absolute configuration is not then the following is used: (+)-(3R, 6S,) or (3S, 6R,) for example.

EXAMPLE 1

Ethyl 2-bromo-5,6,7,8-tetrahydro-6-((4-methoxyphenyl)methyl)quinoline-3-carboxylate a) 2-(2-Cyanopropyl)-4-(4-methoxybenzyl) cyclohexanone 1,4-Dioxospiro[4,5]decan-8-one (45.6 g) was added to a mixture of 4-methoxybenzyl triphenylphosphonium bromide (127.3 g) and epichlorohydrin (100 ml) in toluene (1500 ml) and heated at reflux under a nitrogen atmosphere for 36 hours. The solvent was evaporated under reduced pressure and the residue was extracted into hexane. The hexane solution was evaporated under reduced pressure and the residue distilled at 24° C./1 mmHg to give 8-(4-methoxybenzylidene)- 1,4-dioxaspiro[4,5]-decane, (19 g).

8-(4-Methoxybenzylidene)-1,4-dioxaspiro[4,5]decane (16.5 g) was dissolved in hexane (300 ml) and hydrogenated at atmospheric pressure in the presence of 10% Pd/C (3.5 g). When hydrogen uptake had ended the reaction mixture was filtered through kieselguhr to give, after evaporation of the solvent 8-(4-methoxybenzyl)- 1,4-dioxaspiro[4,5]decane, (16.5 g).

8-(4-Methoxybenzyl)-1,4-dioxaspiro[4,5]decane (47 g) was added to 80% aqueous acetic acid (150 ml) at 65° C. and was left to stir for 2 ½ hours after which time the solvent was evaporated under reduced pressure. The residue was dissolved in ethyl acetate and washed with water. The organic phase was dried (MgSO₄) and evaporated under reduced pressure to give after distillation at 180° C./0.04 mmHg 4-(4-methoxybenzyl)cyclohexanone, (40 g).

b) 4-((4-Methoxyphenyl)methyl)cyclohexanone (3.87 g, prepared as described in Example 1a)) was dissolved in toluene (150 ml) containing morpholine (7.8 ml) and toluene-p-sulphonic acid (0.1 g) and the mixture was heated at reflux. Water generated during the reaction was collected using a Dean and Stark trap. After 18 hours the reaction mixture was evaporated under reduced pressure and when all the morpholine had been removed, the residue was redissolved in toluene (100 ml) and cooled to ice temperature. To this solution was added ethyl 2-cyanoacrylate (5 g)

with rapid stirring. After 18 hours the reaction mixture was evaporated under reduced pressure and the residue dissolved in 85% aqueous acetic acid. After 30 minutes the reaction mixture was diluted with water and extracted into ethyl acetate. The organic phase was dried (MgSO$_4$) and evaporated under reduced pressure. The residue was purified by chromatography, first on silica using ethyl acetate as eluent and then on silica using dichloromethane as eluent. The solvent was evaporated under reduced pressure to give 2-cyano-3-[3-(4-methoxyphenyl)methyl-6-oxocyclohexanyl]propanoic acid ethyl ester (5.14 g).

c) 2-Cyano-3-[3-(4-methoxyphenyl)methyl-6-oxocyclohexanyl]propanoic acid ethyl ester (11.1 g, (prepared as described in step b)) in acetic acid (55 ml) was treated with 30% HBr/acetic acid (11 ml) at room temperature and left for 1½ hours. Aqueous sodium chloride solution was added and the mixture extracted 3 times into methylene dichloride (50 ml). The extracts were washed with dilute Na$_2$CO$_3$ solution (50 ml) and dilute NaCl solution (50 ml), dried (MgSO$_4$) and evaporated to give an oil (11.5 g). The oil was triturated with diethyl ether (50 ml) filtered, washed with diethyl ether and dried to give 3.5 g of ethyl 3,4,5,6,7,8-hexahydro-6-(4-methoxybenzyl)-2-oxo-1[H]-3-quinolinecarboxylate.

d) The mother liquors from the trituration step above were reduced in volume and allowed to crystallise. The solid was filtered off; washed with diethyl ether and dried to give 0.9 g of the title compound. Recrystallisation from 10 ml isopropanol gave 0.6 g of ethyl 2-bromo-5,6,7,8-tetrahydro-6-((4-methoxyphenyl)methyl) quinoline-3-carboxylate mp 115°–116° C.

Analysis: C$_{20}$H$_{22}$BrNO$_3$ requires: C, 59.41; H, 5.48; N, 3.46% Found: C, 59.47; H, 5.63, H, 3.40%.

EXAMPLE 2

2-Bromo-5,6,7,8-tetrahydro-3-hydroxymethyl-6-((4-methoxyphenyl)methyl)quinoline

Ethyl 2-bromo-5,6,7,8-tetrahydro-6-((4-methoxyphenyl)methyl)quinoline-3-carboxylate (2.0 g) (prepared according to Example 1) and THF (20 ml) under a nitrogen atomsphere were treated with 2.0 molar LiBH4/THF (10 mM) and the mixture refluxed for 3 hours. On cooling to room temperature the mixture was poured into water (100 ml) and extracted with CH$_2$Cl$_2$ (2×20 ml) washed with water, dried (MgSO$_4$) and evaporated to give an oil (1.8 g). This was dissolved in isopropanol, acidified to pH 1 with diethyl ether/HCl solution and stirred 1 hour at room temperature. The solution was filtered and washed with diethyl ether and dried to give the hydrochloride of the title compound (1.4. g), mp 178°–180° C.

Analysis: C$_{18}$H$_{20}$BrNO$_2$.0.7 HCl requires: C, 55.75; H, 5.38; N, 3.61% Found: C, 55.86; H, 5.12; N, 3.43%.

EXAMPLE 3

5,6,7,8-Tetrahydro-3-hydroxymethyl-6-((4-methoxyphenyl)methyl)quinoline

A mixture of 2-bromo-5,6,7,8-tetrahydro-3-hydroxymethyl-6-((4-methoxyphenyl)methyl)quinoline (1 g) (prepared according to Example 2) was hydrogenated at 50 psi and room temperature in the presence of sodium methoxide (1 g) in ethanol (50 ml) and 0.1 g of 10% palladium on carbon catalyst. The catalyst was removed by filtration and the solvent evaporated to give a residue. This was treated with water and the product extracted with chloroform. The chloroform extracts were dried (MgSO$_4$) and evaporated to give an oil which crystallised to give a solid (0.78 g). The solid was dissolved in methanol and treated with ethereal HCl. After evaporation of the solvent the residue was triturated with diethyl ether to give the title compound as the hydrochloride salt, mp 168°–170° C.

Analysis: C$_{18}$H$_{21}$NO$_2$.HCl requires: C, 67.9; H, 6.4; N, 4.25% Found: C, 67.6; H, 6.9; N, 4.4%.

EXAMPLE 4

Ethyl 5,6,7,8-tetrahydro-6-((4-methoxyphenyl)methyl)quinolin-3-carboxylate

In a manner analogous to Example 3 ethyl 2-bromo-5,6,7,8-tetrahydro-6-(4-methoxyphenyl)methylquinolin-3-carboxylate (prepared according to Example 1) was hydrogenated at 50 psi at room temperature to give the title compound as the hydrochloride salt, mp 193°–4° C.

Analysis: C$_{20}$H$_{23}$NO$_3$.HCl requires: C, 66.4; H, 6.7; N, 3.9% Found: C, 66.3; H, 6.7; N, 3.8%.

EXAMPLE 5

(E)-7,8-Dihydro-6-(4-methoxyphenyl)methylene-3-methylquinolin-5-[6H]one

A mixture of 7,8-dihydro-3-methylquinolin-5[6H]-one (1 g) and p-methoxybenzaldehyde (0.75 ml) containing 3 drops of piperidine were heated at 100° C. for 2 hours. 2N Hydrochloric acid (25 ml) was added and a solid formed. This was filtered off, washed first with water, then ethanol and then diethyl ether to give the title compound as the hydrochloride, monohydrate m.p 234°–236° C.

Analysis: C$_{18}$H$_{17}$NO$_2$ requires: C, 64.8; H, 6.0; N, 4.2% Found: C, 64.8; H, 6.0; N, 4.1 %.

EXAMPLE 6

7,8-Dihydro-6-((4-methoxyphenyl)methyl)-3-methylquinolin-5-[6H]one

To (E)-7,8-Dihydro-3-methyl-6-(4-methoxyphenyl)methylquinolin-5-[6H]one (1.05 g, prepared according to Example 5) was added triethylsilane (2.4 ml) and then trifluoroacetic acid (1.2 ml). The reaction mixture was quenched with Na$_2$CO$_3$ and dissolved in 2N HCl. The mixture was extracted with ethyl acetate, basified with solid Na$_2$CO$_3$, extracted into chloroform, dried (MgSO$_4$) and evaporated to give a solid. The solid was purified on a silica column using 10% v/v ethyl acetate in CH$_2$Cl$_2$. The title compound having an Rf value 0.36 was collected (0.75 g), mp 92°–93° C.

Analysis: C$_{18}$H$_{19}$NO$_2$ requires: C, 76.8; H, 6.8; N, 5.0% Found: C,76.5; H, 6.9; N, 5.0%.

EXAMPLE 7

7,8.Dihydro-6-hydroxy-6-((4-methoxyphenyl)methyl )-3- methylquinolin-5-[6H]one

The title compound having an Rf value 0.16 was isolated from the silica column purification step of Example 6 (0.2 g) mp 120°–122° C.

Analysis: C$_{18}$H$_{19}$NO$_3$ requires: C, 72.3; H, 6.4; N, 4.7% Found: C, 72.7; H, 6.5; N, 4.7%.

EXAMPLE 8

(±)-5,6,7,8-Tetrahydro-6-((4-methoxyphenyl)methyl)-3-methylquinoline

A mixture of 7,8-dihydro-6-((4-methoxyphenyl)methyl)-3-methylquinolin-5[6H]-one (0.5 g) (prepared as shown in Example 6), potassium t-butoxide (0.64 g); hydrazine hydrate (0.2 ml) in ethylene glycol (5ml) was heated at reflux for 4 hours. After standing for 24 hours the mixture was diluted with water (190 ml) and extracted into t-butylmethyl ether. The extracts were dried ($MgSO_4$) evaporated and purified by column chromatography. The solid obtained was converted to the hydrochloride using ethanolic HCl, dried under vacuum, washed with diethyl ether and filtered to give the hydrochloride of the title compound, 170mg, mp 210°–212° C.

Analysis: $C_{18}H_{21}NO.HCl$ requires: C, 71.1; H, 7.3; N, 4.6% Found: C, 70.7; H, 7.4; N, 4.5%.

EXAMPLE 9

(+)-(6S)5,6,7,8-Tetrahydro-6-((4-methoxyphenyl)methyl)-3-methylquinoline (±)-5,6,7,8-Tetrahydro-6-((4-methoxyphenyl)methyl)-3-methylquinoline prepared according to Example 8 was separated by HPLC using a CHIRALPAK AD Ad 20×250 mm column using hexane:ethanol (95:5 v/v) as mobile phase with a flow rate of 10 ml/mins. Each injection was of 100 microlitres of 70 mg/ml starting material in 1:1 a mixture of hexane and ethanol. The peak which eluted at 24.4 minutes was collected and evaporated to give the title compound, (0.06 g) mp 46°–48° C. $[\alpha]_D^{28}=100°$ (1% $CHCl_3$)

Analysis: $C_{10}H_{21}NO$. $0.1H_2O$ requires: C, 80.3; H, 7.9; N, 5.2% Found C, 80.3; H, 8.1;N, 5.2%.

EXAMPLE 10

(−)-(6R)-5,6,7,8-Tetrahydro-6-((4-methoxyphenyl)methyl)-3-methylquinoline

In the procedure described in Example 9, the peak which eluted at 27.5 minutes was collected and evaporated to give the title compound. (0.06 g).$[\alpha]_D^{28}=95°$ (1% $CHCl_3$)

Analysis: $C_{10}H_{21}NO.0.3H_2O$ requires: C,79.1; H,8.0; N, 5.1% Found: C, 79.2; H, 8.2: N, 5.1%.

EXAMPLE 11

5,6,7,8-Tetrahydro-5-hydroxy-6-((4-methoxyphenyl)methyl)-3-methylquinoline (E)-7,8-Dihydro-6-(4-methoxyphenyl)methylene-3-methylquinolin-5[6H]one (5 g. prepared according to Example 5) was suspended in IPA (20 ml) and sodium borohydride (1.5 g) was added. The mixture was heated at reflux for 3 hours and the solvent was then evaporated and the residue treated with 2N HCl. The acidic solution was washed with diethyl ether and was basified with solid sodium carbonate. The aqueous layer was extracted into ethyl acetate and the organic solution dried ($MgSO_4$) and evaporated under reduced pressure. The residue was recrystallised from diisopropyl ether to give the title compound (4 g).

Analysis: $C_{11}H_{21}NO_2$ requires: C, 76.1; H, 7.8; N, 5.0 Found: C, 76.3; H, 7.5; N, 4.9%.

EXAMPLE 12

(E)-7,8-Dihydro-6-(4-fluorophenyl)methylidine-3-methylquinolin-5-one 7,8-Dihydro-3-methylquinolin-5[6H]one (10 g) was mixed with 4-fluorobenzaldehyde (7.3 ml) and piperidine (0.5 ml). The mixture was heated to 110° C. for 3 hours. The reaction mixture was allowed to cool, diluted with ethyl acetate and extracted into 2N HCl. This aqueous layer was basified with sodium carbonate and extracted into chloroform. This organic solution was dried ($MgSO_4$) and evaporated to give a black tar which was extracted into hexane (4×500 ml). This first aliquot was discarded and the next three were evaporated. The residue was recrystallised from diethyl ether/ hexane to give the title compound (2.9 g), mp 134°–137° C.

Analysis: $C_{17}H_{14}FNO$ requires C, 76.4; H, 5.3; N, 5.2 Found: C, 76.3; H, 5.3; N, 5.3%.

EXAMPLE 13

5,6,7,8-Tetrahydro-6-((4-fluorophenyl)methyl)-5-hydroxy-3-methylquinoline (E)-7,8-Dihydro-6-((4-fluorophenyl )methylidine-3-methylquinolin-5[6H]one (3 g) prepared according to Example 12 was suspended in IPA (50 ml) containing sodium borohydride (1.5 g) and heated at reflux for 3 hours. The reaction mixture was evaporated under reduced pressure and quenched by addition of 2N HCl. The acidic solution was basified with solid $K_2CO_3$ and was extracted into ethyl acetate. The organic phase was dried ($Na_2SO_4$) and evaporated under reduced pressure to give the title compound (2.5 g).

Analysis: $C_{13}H_{18}FNO$ requires C, 75.2; H, 6.7; N, 5.2 Found: C, 75.3; H, 6.7; N, 5.3%

EXAMPLE 14

E-7,8-Dihydro6-(4-cyanophenyl)methylidine-3-methylquinoline-5-one 7,8-Dihydro-3-methylquinolin-5[6H]one (8 g) and 4-cyanobenzaldehyde (4.1 g) were mixed together with piperidine (0.5 ml) and heated at 110° C. for 3 hours. Toluene (50 ml) was added and the mixture heated at reflux under a Dean and Stark trap for 3 hours. The reaction mixture was allowed to cool and crystals formed. These were isolated by filtration and then washed with toluene and then diethyl ether. This solid was recrystallised from ethyl acetate to give the title compound (5.5 g), mp 202°–204° C.

Analysis: $C_{18}H_{14}N_2O$ requires C, 77.8; H, 5.1; N, 10.2 Found: C, 77.8; H, 5.1; N, 10.1%.

EXAMPLE 15

7,8-Dihydro-6-(4-acetamidophenyl)methylidene-3-methylquinolin-5-one 7,8-Dihydro-3-methylquinoline-5[6H]one (8 g) was mixed with 4-acetamidobenzaldehyde (9 g) and piperidine (0.5 ml) and heated at 110° C. for 3 hours. Ethyl acetate (30 ml) was added to the hot reaction mixture and the mixture allowed to cool. Crystals formed and were isolated by filtration, then washed with diethyl ether to give the title compound (11.2 g). A portion was recrystallised from ethyl acetate to give an analytical sample, mp 226°–228° C.

Analysis: $C_{19}H_{18}N_2O_2$ requires: C, 74.5; H, 5.9; N, 9.1 Found: C, 74.2; H, 6.1; H, 9.0%.

EXAMPLE 16

5,6,7,8-Tetrahydro-6-(4-acetamidophenyl)methyl-5-hydroxy-3-methylquinoline (E)-7,8-Dihydro-6-(4-acetamidophenyl)methylidine-3-methylquinolin-5-one (5 g, prepared according to Example 15) was mixed with sodium borohydride (1.5 g) in IPA (50 ml) and heated at reflux for 3 hours. The solvent was removed under reduced pressure and the reaction quenched by addition of 2N HCl. The acidic solution was basified by addition of potassium carbonate, and extracted into ethyl acetate. The organic solution was dried ($Na_2SO_4$) and evaporated. The residue was triturated with diethyl ether to give the title compound, (3.55 g) mp 155°–164° C.

Analysis: $C_{19}H_{22}N_2O_2$ requires C, 73.5; H, 7.1; N, 9.0 Found: C, 73.2; H, 7.5; N, 8.9%.

EXAMPLE 17

5,6,7,8-Tetrahydro-6-(4-fluorophenyl)methyl-3-methylquinoline 5,6,7,8-Tetrahydro-6-((4-fluorophenyl)methyl-5-hydroxy-3-methylquinoline (2.4 g prepared according to Example 13) was dissolved in thionyl chloride (15 ml) and left to stir for 3 hours. The solvent was evaporated the residue diluted with water. The aqueous solution was basified with solid $K_2CO_3$ and extracted into ethyl acetate. The organic solution was dried ($Na_2SO_4$) and evaporated to give 5,6,7,8-tetrahydro-5-chloro-6-(4-fluorophenyl)methyl-3-methylquinoline (2.13 g). This was dissolved in THF (20 ml) and L-Selectride (1M solution in THF, 20 ml) was added. The reaction mixture was left to stir for 20 hours and acetic acid (5 ml) was added. The solvent was evaporated under reduced pressure and the residue dissolved in 2N HCl. The acidic solution was washed with ethyl acetate and basified with solid $K_2CO_3$. The basic solution was extracted into ethyl acetate, dried ($MgSO_4$), evaporated and the residue dissolved in methanol and ethereal hydrogen chloride added. The solvent was evaporated under reduced pressure and the methanol was replaced and evaporated three times. The residue was recrystallised from EPA/ethyl acetate to give the title compound as the monohydrochloride salt (1.12 g), mp=168°–169° C.

Analysis: $C_{17}H_{18}FN.HCl$ requires: C, 70.0; H, 6.6; N, 4.8 Found: C, 69.7; H, 6.8; N, 4.8%.

EXAMPLE 18

5,6,7,8-Tetrahydro-6-(4-cyanophenyl)methyl-5-hydroxy-3-methylquinoline (E)-7,8-Dihydro-6-(4-cyanophenyl)methylidine-3-methylquinoline-5[6H]-one (4 g prepared according to Example 14) was suspended in IPA and sodium borohydride (2.1 g) was added. This mixture was heated at reflux for 3 hours and then evaporated under reduced pressure. The residue was quenched by addition of 2N HCl and then basified with solid sodium carbonate. The basic solution was extracted into ethyl acetate and the organic solution was dried ($MgSO_4$) and evaporated under reduced pressure to give the title compound as a resin (4 g). A sample of this resin was re-crysallised from ethyl acetate to give the title compound, mp 174°–175° C.

Analysis: $C_{18}H_{18}N_2O$ requires: C, 77.7; H, 6.5; N, 10.1 Found: C, 77.4; H, 6.8; N, 10.1%.

EXAMPLE 19

(+)-(6S, 8S)-5,6,7,8-Tetrahydro-8-hydroxy-6-((4-methoxyphenyl)methyl)-3-methylquinoline (+)-(6S)-5,6,7,8-Tetrahydro-6-((4-methoxyphenyl)methyl)-3-methylquinoline-N-oxide (3.48g 0.012 mol) in toluene (40 ml) was added slowly to refluxing acetic anhydride (18 ml) and the mixture stirred for a further 3 hours. After cooling overnight, the reaction mixture was concentrated under reduced pressure and dissolved in methanol. The resulting solution was treated with 5M KOH until it was basic and again concentrated under reduced pressure. The residue was dissolved in water (40 ml) and washed with chloroform (3×40 ml). The combined organic phases were washed with brine (1×40 ml), dried ($MgSO_4$) and concentrated under reduced pressure to give an oil (3.98 g) which solidified on standing. The product (1.9 g) was chromatographed on silica gel eluting with ethyl acetate to give the title compound (0.21 g), $[\alpha]_D^{25}=+115\%$ (1% $CHCl_3$) mp 105°–7° C.

Analysis: $C_{18}H_{21}NO_2$ requires: C, 76.3, H, 7.5; N, 4.9 Found: C, 76.0; H, 7.6; N, 4.9%.

EXAMPLE 20

(+)-(6S,8R)-5,6,7,8-Tetrahydro-8-hydroxy-6-((4-methoxyphenyl)methyl)-3-methylquinoline (+)-(6S)-5,6,7,8-Tetrahydro-6-((4-methoxyphenyl)methyl)-3-methylquinoline-N-oxide (4.45 g, 0.016 mol) in toluene (40 ml) was added slowly to refluxing acetic anhydride (20 ml) and the reaction mixture stirred for a further 3 hours. After cooling overnight, the mixture was concentrated under reduced pressure and dissolved in methanol. The resulting solution was treated with 5M KOH until it was basic and again concentrated under reduced pressure. The residue was dissolved in water (45 ml) and washed with chloroform (3×40 ml). The combined organic phases were washed with brine (1×40 ml) and water (1×40 ml), dried ($MgSO_4$) and concentrated under reduced pressure to give an oil (5.46 g). The oil was chromatographed on silica gel eluting with ethyl acetate/hexane (1:1) to give a white solid (1 g) which was recrystaulised from diisopropyl ether/acetonitrile to give the title compound as a white crystalline solid, 0.63 g. $[\alpha]_D^{26}=+68°$ (1% $CHCl_3$), mp 132°–4° C.

Analysis: $C_{18}H_{21}NO_2.0.25H_2O$ requires: C, 75.1; H, 7.5; N, 4.9 Found: C, 75.4; H, 7.5; N, 4.9%.

EXAMPLE 21

(+)-(6S,8S)-5,6,7,8-Tetrahydro-6-((4-methoxyphenyl)methyl)-3,8-dimethylquinoline N-Butyllithium (2.9 ml, 1.43 m) was added slowly to a stirred solution of (+)-(6S)-5,6,7,8-tetrahydro-6-((4-methoxyphenyl)methyl-3-methylquinoline (1 g, 0.004 mol) in THF (10 ml) at 40° C. The mixture was stirred for a further 10 minutes and a solution of methyl iodide (0.58 g 0.004 mol) in THF (5 ml) was slowly added. The resulting reaction mixture was allowed to warm to room temperature overnight. Water (30 ml) was added and the mixture concentrated under reduced pressure. The aqueous phase was washed with ethyl acetate (3×30 ml) and the combined organic phases were washed with brine (1×30 ml), water (1×30 ml), dried ($MgSO_4$) and concentrated under reduced pressure to give an oil (1.24 g). The oil was chromatographed on silica gel eluting with ethyl acetate to afford two fractions. The first fraction was evaporated to give an oil, 0.34 g, which was dissolved in cyclohexane and treated with ethereal hydrochloric acid to give a cloudy solution. This was concentrated under reduced pressure to afford an oil which was triturated with ethyl acetate to give the hydrochloride salt of the title compound as a colourless powder, yield: 0.07 g, $[\alpha]_D^{27}=+91°$ (1% $CHCl_3$) mpt 162°–4° C.

Analysis $C_{19}H_{23}NO.HCl$ requires: C, 71.8; H, 7.6; N, 4.4 Found C, 71.4; H, 7.7; N, 4.2%.

EXAMPLE 22

(+)-(6S,8R)-5,6,7,8-Tetrahydro-6-((4-methoxyphenyl)-methyl)-3,8-dimethylquinoline The second fraction obtained from the procedure of Example 21 (0.303 g) was evaporated to give an oil which was dissolved in ethyl acetate and treated with ethereal hydrochoric acid. The solid (0.23 g) produced was recrystallised from ethyl acetate/acetonitrile to give a colourless solid, yield=0.09 g. $[\alpha]_D^{27}=+61°$ (1% $CHCl_3$) mpt 218°–222° C.

Analysis: $C_{19}H_{23}NO.HCl$ requires: C, 71.8; H, 7.6; N, 4.4 Found: C,71.6; H, 7.7; N, 4.4%.

EXAMPLE 23

(+)-(6S,8S)-5,6,7,8-Tetrahydro-6-((4-methoxyphenyl)methyl)-8-hydroxymethyl-3-methyyquinoline A) N-Butyl lithium (8.7 ml, 1.43M) was slowly added to a cooled (−40° C.) solution of (6S )-5,6,7,8-tetrahydro-6-((4-methoxyphenyl methyl)-3-methyl-quinoline (3.0 g, 11.0 mmol) in tetrahydrofuran (30 ml). The reaction was stirred for a further 15 minutes and a solution of 2-(trimethylsilydethoxymethyl chloride (2.06 g, 12.0 mmol) in tetrahydrofuran (20 ml) was added slowly. The reaction mixture was left stirring overnight, concentrated under reduced pressure and then poured into dilute hydrogen chloride (2M, 90 ml). The acidic phase washed with ethyl acetate (3×70 ml) and the combined organic phases washed with brine (70 ml), dried ($MgSO_4$) and concentrated under reduced pressure to afford an oil. Yield 5.0 g.

B) Boron trifluoride etherate (15 ml) was slowly added to a cooled (0° C.) solution of (6S,8S)-5,6,7,8-tetrahydro-6-( (4-methoxyphenyl)methyl)-8-(2-trimethylsilylethoxymethyl)-3-methylquinoline (5.0 g, 12.6 mmol) in dichloromethane (100 mnl). The reaction mixture was stirred for a further 3.5 hours and saturated sodium bicarbonate added. The organic phase was washed with sodium bicarbonate (3×75 ml), dried ($MgSO_4$) and concentrated to afford an oil (3.36 g). The crude product was chromatographed on silica gel eluting with ethyl acetate: hexane (1:1 to 2:1) to afford two fractions a) and b):

(a) The first, an oil, was chromatographed on alumina gradient eluting with ethyl acetate: hexane (1:3 to 1:1) to afford two fractions:

A1 Colourless solid (starting material)—0.56 g

A2 Colourless solid (1.52 g)—this was recrystallised from cyclohexane to give the title compound, yield 0.55 g, mp 88°–91° C, . $[\alpha]_D^{27}=+104°$ (1% $CHCl_3$).

Analysis: $C_{19}H_{23}NO_2$ requires: C, 76.7; H, 7.8; N, 4.7 Found: C, 76.7; H.7.8; H, 4.7%.

(b) The second, an oil, was chromatographed on alumina, eluting with ethyl acetate: hexane (1:1) to give a fraction containing 93–94% of the trans isomer, yield 0.36 g.

EXAMPLE 24

(+)-(6S,8R)-5,6,7,8-Tetrahydro-8-acetoxy-6-((4-methoxyphenyl)methyl)-3-methylquinoline Diisopropylethylamine (0.43 g, 33, $10^{-3}$ mol), a catalytic amount of 4-dimethylarminopyridine and a solution of acetyl chloride (0.26 g, 33×$10^{-3}$ mol) in dichloromethane (5 ml) were added slowly to a solution of (6S,8R)-5,6,7,8-tetrahydro-8-hydroxy-6-((4-methoxyphenylmethyl)-3-methylquinoline (0.94 g), 33×$10^{-3}$ mol) in dichloromethane (7 ml) at room temperature. The mixture was stirred overnight before further additions of acetyl chloride (0.21 g 0.0015 mol) and diisopropylamine (0.21 g, 0.0015 mol) were made. The mixture was again stirred overnight then diluted with dichloromethane (15 ml) and washed with water (1×15 ml), sodium hydrogen carbonate (1×15 ml), brine (1×15 ml) and water (1×15 ml). After drying ($MgSO_4$) the reaction mixture was concentrated under reduced pressure to give an oil (1.1 g). The crude product was chromatographed on silica gel eluting with ethyl acetate to give the title compound as the hemihydrate, (0.76 g), $[\alpha]_D^{26}=+72°$ (1% $CHCl_3$) mp 94°–8° C.

Analysis $C_{20}H_{23}NO_3.½H_2O$ requires: C, 71.9, H, 7.2; N, 4.2% Found C, 71.9; H, 7.0; N, 4.2%.

EXAMPLE 25

(+)-(6S)-5,6,7,8-Tetrahydro-6-((4-methoxyphenyl) methyl)-3-methylquinoline N-oxide A solution of (+)-(6S)-5,6,7,8-tetrahydro-6-((4-methoxyphenyl)methyl)-3-methyl-quinoline (2 g 7.5×$10^{-3}$ mol, prepared according to Example 9) in dichloromethane (10 ml) was added slowly to a stirred solution of m-chloroperoxybenzoic acid (1.78 g 8.3×$10^{-3}$ mol) at room temperature. After stirring overnight the reaction mixture was concentrated under reduced pressure and aqueous dilute sodium hydroxide (2 m, 20 ml) was added to the residue which was then washed with chloroform (3×15 ml). The aqueous phase was saturated with sodium chloride, washed with chloroform (3×15 ml) and the combined organic phases dried ($MgSO_4$) and concentrated under reduced pressure to afford a solid (2.36 g). This was recrystallised twice from diisopropylether/acetonitrile to give the title compound, (0.38 g), mp 138°–142° C., $[\alpha a]_D^{24}=+57°$ (1% $CHCl_3$).

Analysis: $C_{18}H_2NO_2$ requires: C, 75.8; H, 7.5; N, 4.9 Found: C, 75.8; H, 7.5; N, 4.8%.

EXAMPLE 26

(+)-(6S,7S)-5,6,7,8-Tetrahydro-7-(O-benzylhydroxylamino-6-((4-methoxyphenyl)methyl) -3-methylquinoline (A) (6S)-5,6,7,8-Tetrahydro-6-((4-methoxyphenyl) methyl))-8-hydroxy-3-methylquinoline (2.0 g, 7.1 mmoles, prepared according to Example 19/20) was added slowly to stirred hot (100° C.) polyphosphoric acid (19 g) and stirring continued for a further 1.5 hours after which time the mixture was poured into water (50 ml). The acidic solution was basified with concentrated ammonia and washed with chloroform (4×50 ml). The combined chloroform extracts were washed with brine (50 ml) then water (50 ml), dried ($MgSO_4$) and concentrated to afford an oil (1.76 g). The oil was chromatographed on alumina eluting with hexane:ethyl acetate (4:1 to 1:1) to give a fraction (0.87 g) which contained 40% of (6S)-5,6-dihydro-6-((4-methoxyphenyl) methyl)-3-methylquinoline.

(B) O-Benzylhydroxylamine hydrochloride (0.27 g, 1.7 mmol) was added slowly to a solution of the product of step (A) (0.87 g, 40% pure, 1.70 mmoles) in methanol (5 ml). The reaction mixture was stirred overnight and then heated under reflux for 4 hours. On cooling the reaction mixture was diluted with ethyl acetate (30 ml). The ethyl acetate extract was washed with dilute sodium hydroxide (15 ml), brine (15 ml) and water (15 ml), dried ($MgSO_4$) and concentrated to afford an oil (0.95 g). This was chromatographed on silica gel, eluting with ethyl acetate: hexane (2:1) to afford a fraction which on evaporation gave 0.24 g of a solid. This was recrystallised from cyclohexane (5 ml) to give the title compound, mp 98°–101° C., $[\alpha]_D^{25}=+50°$ (1% CHCl$_3$).

Analysis: $C_{25}H_{28}N_2O_2$ requires: C, 77.3; H, 7.3; N, 7.2 Found: C, 77.2; H, 7.2; N, 7. 1%.

EXAMPLE 27

(+)-(6S,8S)-5,6,7,8-Tetrahydro-8-acetoxy-6-((4-methoxyphenyl)methyl )-3 -methylquinoline Diisopropylethylamine (0.51 g, 3.9 mmol), a catalytic amount of 4-dimethylaminopyridine and a solution of acetyl chloride (0.31 g, 3.9 mmol) in dichloromethane (5 ml) were added slowly to a solution of 5,6,7, 8-tetrahydro-8-hydroxy-6-((4-methoxyphenyl)methyl)-3-methylquinoline (1.12 g, 3.9 mmol) in dichloromethane (7 ml) at room temperature. The mixture was stirred overnight before further additions of acetyl chloride (0.32 g, 4 mmol) and diisopropylethylamine (0.51 g, 4 mnmol) were made. The mixture was again stirred overnight then diluted with dichloromethane (15 ml) and washed with water (1×15 ml), sodium hydrogen carbonate (1×15 ml), brine (1×15 ml) and water (1×15 ml). After drying (MgSO$_4$) the reaction mixture was concentrated under reduced pressure to give an oil (1.46 g). This product was chromatographed on silica gel eluting with ethyl acetate/hexane (1:1) to give a fraction which on evaporation gave a solid (0.8 g). The solid was recrystallised from hexane to afford the title compound, (0.45 g), mp 113°–115° C., $[\alpha]_D^{27}=+46°$ (1%CHCl$_3$).

Analysis: $C_{20}H_{23}NO_3 \cdot \frac{1}{4}H_2O$ requires: C, 72.8; H, 7.2; N, 4.3 Found: C, 73.0; H, 7.0; N, 4.2%.

EXAMPLE 28

5,6,7,8-Tetrahydro-6-((4-aminomethylphenvy) methyl )-3-methylquinoline 5,6,7,8-Tetrahydro-6-((4-cyanophenyl)methyl)-5-hydroxy-3-methylquinoline (2.15 g, prepared according to Example 18) was dissolved in thionyl chloride (10 ml) and stirred for 3 hours. The solvent was removed under reduced pressure and the residue treated with water (100 ml). The aqueous solution was basified with solid sodium carbonate and extracted into ethyl acetate. The organic solution was dried (MgSO$_4$) and evaporated to give a mixture of 85% 5,6,7,8-tetrahydro-5-chloro-6-(4-cyanophenyl)methyl-3-methylquinoline and 15% 7,8-dihydro-6-(4-cyanophenyl) methyl-3-methylquinoline (2.1 g). This mixture (2 g) was dissolved in THF (20 ml), cooled to 0° C. and 1M lithium tri-s-butyl borohydride in THF (15 ml) was added, followed by a further 15 ml after 24 hours. After 24 hours the reaction was quenched with acetic acid (2 ml) followed by 2N HCl and then washed with t-butyl methyl ether. The aqueous phase was basified with solid sodium carbonate, extracted into chloroform, and the organic phase was dried (MgSO$_4$) and evaporated. The residue was dissolved in methanol (500 ml) and ethereal hydrogen chloride (5 ml) added. The solution was evaporated under reduced pressure and the residue was dissolved in water and was basified with sodium carbonate. The aqueous solution was extracted in chloroform, dried (MgSO$_4$) and evaporated to give the title compound (1.8 g). The crude product was purified by chromatography on silica using ethyl acetate, followed by gradient elution with ethyl acetate/ethanol. The fractions eluting in 100% ethanol was collected, evaporated and the residue was further purified by chromatography on silica using 10% methanol in chloroform as eluent. The residue was dissolved in IPA and was treated with ethereal hydrogen chloride. The solvent was evaporated and the residue dissolved in the minimum volume of methanol and was applied to a 2 mm 'chromatotron' plate. The hydrochloride was purified by elution with 10% ethanol in ethyl acetate The solvent was evaporated under reduced pressure to give the title compound 0.15 g, mp 158°–63° C.

Analysis: $C_{18}H_{22}N_2 \cdot HCl \cdot H_2O$ requires: C, 67.4; H, 7.9; N, 8.7 Found: C, 67.8; H, 7.6; N, 8.7%.

EXAMPLE 29

(+)-(6S)-5,6,7,8-Tetrahydro-6-(4-hydroxyphenylmethyl)-3-methylquinoline (+)-(6S)-5,6,7(8-Tetrahydro-6-(4-methoxyphenyl) methyl-3-methylquinoline (0.47 g) prepared according to Example 9 was heated at reflux in 43% HBr in acetic acid (20 ml) for 5 hours. The reaction mixture was evaporated to dryness and the residue was diluted with saturated aqueous sodium bicarbonate. The aqueous mixture was extracted in ethyl acetate and the organic solution was dried (MgSO$_4$) and evaporated under vacuum. The residue was purified by chromatography on silica using ethyl acetate as eluant. The solution was evaporated under reduced pressure and the residue was recrystallised from ethyl acetate to give the title compound, (0.2 g), mp 157°–158° C., [ $\alpha]_D^{26}=96°$ (1% MeOH). Analysis: $C_{17}H_{19}NO \cdot 0.25H_2O$ requires: C, 79.2; H, 7.6; N, 5.4 Found: C, 79.3; H, 7.4; N, 5.4%.

EXAMPLE 30

(−)-(6R)-5,6,7,8-Tetrahydro-6-(4-hydroxyphenyl) methyl-3-methylguinoline (−)-(6R)-5,6,7,8-Tetrahydro-6-(4-methoxyphenyl) methyl-3-methylquinolline (0.5 g) prepared according to Example 10 was dissolved in 45% HBr in acetic acid (20 ml) and heated at reflux for 25 hours. The reaction mixture was evaporated under reduced pressure, basified with saturated sodium hydrogen carbonate solution and the mixture extracted into ethyl acetate. The organic solution was washed with brine, dried (MgSO$_4$) and then evaporated. The residue was recrystallised from ethyl acetate to give the title compound (0.22 g), mp 159°–160° C. $[\alpha]_D^{26}=-93°$ (1% CHCl$_3$).

Analysis: $C_{17}H_{19}NO \cdot \frac{1}{4}H_2O$ requires: C, 79.2; H, 7.6; N, 5.4 Found: C, 79.5; H, 7.3; N, 5.4%.

We claim:

1. A compound of the generic formula:

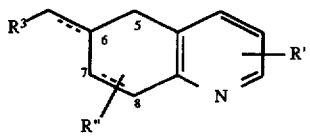

or a pharmaceutically acceptable salt thereof, where the dotted lines represent optional bonds, R$^3$ is C$_6$–C$_{10}$ aryl optionally substituted by one or more substituents, the same or different, selected from C$_1$–C$_6$ alkyl, C$_1$–C$_6$ alkoxy, halogen, halo C$_1$–C$_6$ alkyl, halo C$_1$–C$_6$ alkoxy, carboxy, hydroxy(C$_1$–C$_6$)alkyl, (C$_1$–C$_6$alkoxy)carbonyl, amino, mono- or di-(C$_1$–C$_6$ alkyl)-amino, nitro, hydroxy, mercapto, C$_1$–C$_6$alkylthio, (C$_1$–C$_6$)alkyl carbonyl, (C$_2$–C$_7$)

alkanoyloxy, (C$_1$–C$_6$)alkylcarbonylamino, (C$_2$–C$_7$) alkoxycarbonylamino, cyano, C$_1$–C$_6$ aminoalkyl, and C$_1$–C$_2$ alkylenedioxy;

R' represents one or more optional substituents the same or different, selected from halogen, C$_1$–C$_6$ alkyl, C$_2$–C$_7$ alkoxycarbonyl, C$_1$–C$_6$ hydroxyalkyl, CN, aminocarbonyl, C$_2$–C$_7$ alkanoyloxy(C$_1$–C$_6$)alkyl, carboxy, C$_2$–C$_7$ alkanoxylamino, optionally substituted C$_6$–C$_{10}$ aryl or heteroaryl or an optionally substituted (C$_6$–C$_{10}$ aryl)alkyl or a heteroaryl alkyl radical; said heteroaryl group containing 5 to 10 ring atoms of which one to three of said atoms are heteroatoms selected from oxygen, nitrogen and sulphur, the same or different; said aryl or heteroaryl radicals being optionally substituted by one or more substituents the same or different selected from C$_1$–C$_6$ alkyl, C$_1$–C$_6$ alkoxy, or such groups substituted by C$_6$–C$_{10}$ aryl or heteroaryl as defined above, halogen, halo C$_1$–C$_6$ alkyl, halo C,-C$_6$ alkoxy, carboxy, hydroxy(C$_1$–C$_6$)alkyl C$_2$–C$_7$ alkanoyloxy(C$_1$–C$_6$)alkyl, (C$_1$–C$_6$alkoxy)carbonyl, amino, mono- or di- (C$_1$–C$_6$ alkyl)-amino, nitro, hydroxy, mercapto, C$_1$–C$_6$alkylthio, (C$_1$–C$_6$alkyl)carbonyl, (C$_6$–C$_{10}$ aryl)carbonyl, (C$_2$–C$_7$)alkanoyloxy, (C$_7$–C$_{11}$)aroyloxy, (C$_1$–C$_6$alkyl)carbonylamino, (C$_6$–C$_{10}$aryl)carbonylamino, (C$_2$–C$_7$ alkoxycarbonyl) amino, C$_6$–C$_{10}$ aryl, heteroaryl as defined above, and C$_1$–C$_2$ alkylenedioxy;

R" represents one or more optional mono- or di- valent substituents in the 5, 7 or 8 positions the same or different; monovalent substituents being selected from the following: C$_1$–C$_6$ alkyl, C$_2$–C$_7$ alkanoyloxy, hydroxy, amino, C$_2$–C$_7$ alkanoylamino, C$_1$–C$_6$alkylanino, C$_1$–C$_6$ hydroxalkyl, halogen, C$_7$–C$_{17}$ aralkyloxyamino; and R" can also represent hydroxy in the 6 position when the optional bond is absent; the di-valent substituents being selected from oxo and methylene; and the N-oxides thereof;

with a proviso that when R$^3$ together with the carbon to which it is attached forms unsubstituted benzyl, then R" cannot be an oxo group at the 5-position when R' is hydrogen, and when R$^3$ together with the carbon to which it is attached forms unsubstituted benzylidene, then R' cannot be C$_1$–C$_6$ alkyl.

2. A compound having the formula

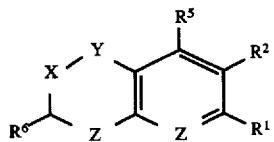

(IA)

wherein

R' is H, halogen, C$_1$–C$_6$ alkyl, optionally substituted C$_6$–C$_{10}$ aryl or heteroaryl or an optionally substituted (C$_6$–C$_{10}$ aryl)alkyl or heteroarylalkyl radical; said heteroaryl group containing 5 to 10 ring atoms of which one or more of said atoms are heteroatoms selected from oxygen, nitrogen and sulphur, the same or different; said aryl or heteroaryl radicals being optionally substituted by one or more substituents the same or different, selected from C$_1$–C$_6$ alkyl, C$_1$–C$_6$ alkoxy, or such groups substituted by C$_6$–C$_{10}$ aryl or heteroaryl as defined above, halogen, halo C$_6$–C$_6$ alkyl, halo C$_1$–C$_6$ alkoxy, carboxy, hydroxy(C$_1$–C$_6$)alkyl, (C$_6$–C$_6$alkoxy) carbonyl, amino, mono- or di(C$_1$–C$_6$ alkyl)-amino, nitro, hydroxy, mercapto, C$_1$–C$_6$alkylthio, (C$_1$–C$_6$) alkylcarbonyl, (C$_6$-C$_{10}$ aryl)carbonyl, (C$_2$-C$_7$) alkanoyloxy, (C$_7$–C$_{11}$)aroyloxy, (C$_1$–C$_6$) alkylcarbonylamino, (C$_6$-C$_{10}$aryl)carbonylamino, (C$_2$–C$_7$) alkoxycarbonylamino, C$_6$–C$_{10}$ aryl, heteroaryl as defined above, and C$_1$–C$_2$ alkylenedioxy;

R$^2$ is hydrogen, C$_1$–C$_6$ alkyl, C$_1$–C$_6$ hydroxyalkyl, C$_2$–C$_7$ alkanoyloxy(C$_1$–C$_6$)alkyl, C$_2$–C$_7$ alkoxycarbonyl, cyano, aminocarbonyl, carboxy or C2-C$_7$ alkanoylarnino;

X is a group of formula:

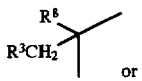 (vii)

or

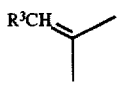 (viii)

where R$^8$ is H or OH;

R$^3$ is a C$_6$–C$_{10}$ aryl radical optionally substituted by one or more substituents, the same or different, selected from C$_1$–C$_6$ alkyl, C$_1$–C$_6$ alkoxy, halogen, halo C$_1$–C$_6$ alkyl, halo C$_1$–C$_6$ alkoxy, carboxy, hydroxy(C$_1$–C$_6$) alkyl, (C$_1$–C$_6$alkoxy)carbonyl, amino, mono- or di(C$_1$–C$_6$ alkyl)-amino, nitro, hydroxy, mercapto, C$_1$–C$_6$alkylthio, (C$_1$–C$_6$)alkylcarbonyl, (C$_2$–C$_7$) alkanoyloxy, (C$_1$–C$_6$)alkylcarbonylamino, (C$_2$–C$_7$) alkoxycarbonylamino, and C$_1$–C$_2$ alkylenedioxy;

Y is

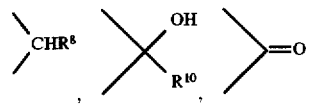

where R$^9$ represents hydrogen, C$_1$–C$_6$ alkyl, C$_2$–C$_7$ alkanoyloxy, optionally substituted heteroaryl, optionally substituted C$_6$–C$_{10}$ aryl or CH$_2$OH; and R$^{10}$ represents hydrogen or C$_1$–C$_6$ alkyl;

Z is C=O, C=CH$_2$, —CHR$^7$— or =C(R$^7$)— where R$^7$ is hydrogen, OH, CH$_2$OH, NH2, C$_2$–C$_7$ alkanoyloxy, C$_2$–C$_7$ alkanoylamino, C$_1$–C$_6$alkylarino or a C$_1$–C$_6$ alkyl group optionally substituted by a group R$^3$ as defined above;

R$^5$ is hydrogen, C$_1$–C$_6$ alkyl, C$_6$–C$_{10}$ aryl, heteroaryl or a C$_1$–C$_6$alkyl substituted by C$_6$–C$_{10}$ aryl or heteroaryl; said aryl or heteroaryl groups being optionally substituted as defined for R$^1$ above and R$^6$ is NH$_2$, C$_7$–C$_{17}$ aralkyloxyamino, C$_2$–C$_7$ alkanoylamino or R$^6$ is one of the values listed for R$^5$ above;

with the proviso that when X is

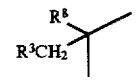

where R$^8$ is H and R$^3$ is unsubstituted phenyl and Y is

where R$^9$ is H, then both R$^1$ and R$^2$ cannot be H, and when X is

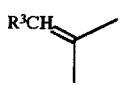

where $R^3$ is unsubstituted phenyl, then Y cannot be

when $R^1$ is $C_1$–$C_6$ alkyl and $R^2$ is H.

3. A compound as claimed in claim 2 having formula (H)

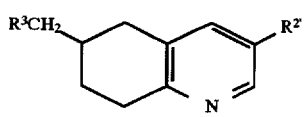

in which formula $R^{2'}$ is hydrogen, $C_1$–$C_6$ alkyl, $C_2$–$C_7$ alkoxycarbonyl, acetylamino, CN or $CH_2OH$ and $R^3$ is a $C_6$–$C_{10}$ aryl group optionally substituted by one or more substituents, the same or different, selected from $C_1$–$C_6$ alkyl, $C_1$–$C_6$ alkoxy, halogen, halo $C_1$–$C_6$ alkyl, halo $C_1$–$C_6$alkoxy, carboxy, hydroxy($C_1$–$C_6$)alkyl, ($C_1$–$C_6$alkoxy)carbonyl, amino, mono- or di- ($C_1$–$C_6$ alkyl)-amino, nitro, hydroxy, mercapto, $C_1$–$C_6$alkylthio, ($C_1$–$C_6$) alkyl carbonyl, ($C_2$–$C_7$)alkanoyloxy, (Cl–$C_6$) alkylcarbonylamino, ($C_2$–$C_7$)alkoxycarbonylamino, cyano, $C_1$–$C_6$ aminoalkyl, and $C_1$–$C_2$ alkylenedioxy; with a proviso that when $R^3$ is unsubstituted phenyl, then $R^2$ cannot be H.

4. A pharmaceutical composition comprising a compound of formula I

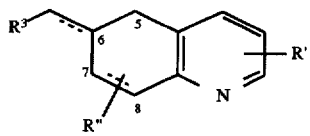

or a pharmaceutically acceptable salt thereof, where the dotted lines represent optional bonds, $R^3$ is $C_6$–$C_{10}$ aryl optionally substituted by one or more substituents the same or different, selected from $C_1$–$C_6$ alkyl, $C_1$–$C_6$ alkoxy, halogen, halo $C_1$–$C_6$ alkyl, halo $C_1$–$C_6$ alkoxy, carboxy, hydroxy($C_1$–$C_6$)alkyl, ($C_1$–$C_6$alkoxy)carbonyl, amino, mono- or di- ($C_1$–$C_6$ alkyl)-amino, nitro, hydroxy, mercapto, $C_1$–$C_6$alkylthio, ($C_1$–$C_6$)alkyl carbonyl, ($C_2$–$C_7$) alkanoyloxy, ($C_1$–$C_6$)alkylcarbonylamino, ($C_2$–$C_7$) alkoxycarbonylamino, cyano, $C_1$–$C_6$ aminoalkyl, and $C_1$–$C_2$ alkylenedioxy;

R' represents one or more optional substituents the same or different, selected from the following: halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxylamino, optionally substituted $C_6$–$C_1$, or heteroaryl or an optionally substituted ($C_6$–$C_{10}$ aryl)alkyl or a heteroaryl alkyl radical; said heteroaryl group containing 5 to 10 ring atoms of which one to three of said atoms are heteroatoms selected from oxygen, nitrogen and sulphur, the same or different; said aryl or heteroaryl radicals being optionally substituted by one or more substituents the same or different selected from $C_1$–$C_6$ alkyl, $C_1$–$C_6$ alkoxy, or such groups substituted by $C_6$–$C_{10}$ aryl or heteroaryl as defined above, halogen, halo $C_1$–$C_6$ alkyl, halo $C_1$–$C_6$ alkoxy, carboxy, hydroxy($C_1$–$C_6$)alkyl, $C_2$–$C_7$ alkanoyloxy($C_1$–$C_6$)alkyl, ($C_1$–$C_6$alkoxy) carbonyl, amino, mono- or di- ($C_1$–$C_6$ alkyl)-amino, nitro, hydroxy, mercapto, $C_1$–$C_6$alkylthio, ($C_1$–$C_6$alkyl)carbonyl, ($C_6$–$C_{10}$ aryl)carbonyl, ($C_2$–$C_7$) alkanoyloxy, ($C_7$–$C_1$,)aroyloxy, ($C_1$–$C_6$alkyl) carbonylamino, ($C_6$–$C_{10}$aryl)carbonylamino, ($C_2$–$C_7$ alkoxycarbonyl)amino, $C_6$–$C_{10}$ aryl, heteroaryl as defined above, and $C_1$–$C_2$ alkylenedioxy;

R" represents one or more optional mono- or di- valent substituents in the 5, 7 or 8 positions the same or different: monovalent substituents being selected from the following: $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxalkyl, halogen, $C_7$–$C_{17}$ aralkyloxyamino; and R" can also represent hydroxy in the 6 position when the optional bond is absent; the di-valent substituents being selected from oxo and methylene;

and/or the N-oxides thereof, and a pharmaceutically acceptable carrier.

5. A method of treating disorders in a mammal amenable to treatment with a potassium ion channel blocking compound which comprises administration to a mammal in need of such treatment a therapeutically effective amount of a compound of formula I

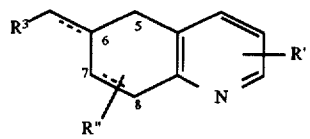

or a pharmaceutically acceptable salt thereof, where the dotted lines represent optional bonds, wherein $R^3$ is $C_6$-$C_{10}$ aryl optionally substituted by one or more substituents the same or different, selected from $C_1$–$C_6$ alkyl, $C_1$–$C_6$ alkoxy, halogen, halo $C_1$–$C_6$ alkyl, halo $C_1$–$C_6$ alkoxy, carboxy, hydroxy($C_1$–$C_6$)alkyl, ($C_1$–$C_6$alkoxy)carbonyl, amino, mono- or di- ($C_1$–$C_6$ alkyl)-amino, nitro, hydroxy, mercapto, $C_1$–$C_6$alkylthio, ($C_1$–$C_6$)alkyl carbonyl, ($C_2$–$C_7$) alkanoyloxy, ($C_1$–$C_6$)alkylcarbonylamino, ($C_2$–$C_7$) alkoxycarbonylamino, cyano, $C_1$–$C_6$ aminoalkyl, and $C_1$–$C_2$ alkylenedioxy;

R' represents one or more optional substituents the same or different, selected from the following: halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxylamino, optionally substituted $C_6$–$C_1$, aryl)alkyl or a heteroaryl alkyl radical; said heteroaryl group containing 5 to 10 ring atoms of which one to three of said atoms are heteroatoms selected from oxygen, nitrogen and sulphur, the same or different; said aryl or heteroaryl radicals being optionally substituted by one or more substituents the same or different selected from $C_1$–$C_6$ alkyl, $C_1$–$C_6$ alkoxy, or such groups substituted by $C_6$–$C_{10}$ aryl or heteroaryl as defined above, halogen, halo $C_1$–$C_6$ alkyl, halo $C_1$–$C_6$ alkoxy, carboxy, hydroxy($C_1$–$C_6$)alkyl, $C_2$–$C_7$ alkanoyloxy($C_1$–$C_6$)alkyl, ($C_1$–$C_6$alkoxy) carbonyl, amino, mono- or di- ($C_1$–$C_6$ alkyl)-amino, nitro, hydroxy, mercapto, $C_1$–$C_6$alkylthio, ($C_1$–$C_6$alkyl)carbonyl, ($C_6$–$C_{10}$ aryl)carbonyl, ($C_2$–$C_7$) alkanoyloxy, ($C_7$–$C_1$,)aroyloxy, ($C_1$–$C_6$alkyl)

carbonylamino, ($C_6$–$C_{10}$aryl)carbonylamino, ($C_2$–$C_7$ alkoxycarbonyl)amino, $C_6$–$C_{10}$ aryl, heteroaryl as defined above, and $C_1$–$C_2$ alkylenedioxy;

R" represents one or more optional mono- or di- valent substituents in the 5, 7 or 8 positions the same or different: monovalent substituents being selected from the following: $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxyalkyl, halogen, $C_7$–$C_{17}$ aralkyloxyamino; and R" can also represent hydroxy in the 6 position when the optional bond is absent; the di-valent substituents being selected from oxo and methylene;

and the N-oxides thereof.

6. A compound as claimed in claim 2 wherein X has formula (vii) wherein $R^8$ is hydrogen.

7. A compound as claimed in claim 2 wherein Y is $CH_2$.

8. A compound as claimed in claim 2 wherein Z is $CH_2$.

9. A compound as claimed in claim 2 wherein $R^1$, $R^5$ and $R^6$ are hydrogen.

10. A compound as claimed in claim 2 wherein $R^2$ is hydrogen, $C_1$–$C_6$ alkyl, $C_2$–$C_7$ alkoxycarbonyl, $C_2$–$C_7$ alkanoylamino, CN or $CH_2OH$.

11. A compound as claimed in claim 1 wherein $R^3$ is substituted or unsubstituted phenyl wherein the substituent (s) is/are selected from one or more of the following the same or different: $C_1$–$C_6$ alkyl, $C_1$–$C_6$ alkoxy, hydroxy, halogen and methylene- or ethylene-dioxy.

12. A compound of claim 1 which is ethyl 2-bromo-5,6,7,8-tetrahydro-6-((4-methoxyphenyl)methyl)quinoline-3-carboxylate or a pharmaceutically acceptable salt therof.

13. A compound of claim 1 which is 2-bromo-5,6,7,8-tetrahydro-3-hydroxymethyl-6-((4-ethoxyphenyl)methyl)quinoline or a pharmaceutically acceptable salt therof.

14. A compound of claim 1 which is 3-hydroxymethyl-6-((4methoxyphenyl)methyl)-5,6,7,8-tetrahydroquinoline or a pharmaceutically acceptable salt therof.

15. A compound of claim 1 which is ethyl 5,6,7,8-tetrahydro-6-((4-methoxyphenyl)methyl)quinolin-3-carboxylate or a pharmaceutically acceptable salt therof.

16. A compound of claim 1 which is 5,6,7,8-tetrahydro-6-((4-methoxyphenyl)methyl)-3-methylquinoline or a pharmaceutically acceptable salt therof.

17. A compound of claim 1 which is 7,8-dihydro-6-(4-methoxyphenyl)methylene-3-methylquinolin-5[6H]-one or a pharmaceutically acceptable salt therof.

18. A compound of claim 1 which is 7,8-dihydro-6-((4-methoxyphenyl)methyl)-3-methylquinolin-5[6H]-one or a pharmaceutically acceptable salt therof.

19. A compound of claim 1 which is 7,8,dihydro-6-hydroxy-6-((4-methoxyphenyl)methyl)-3-methylquinolin-5[6H]-one or a pharmaceutically acceptable salt therof.

20. The method of treatment according to claim 5 wherein the disorder treated is depression, pain, psychoses, cognitive disorder, impaired memory and learning, anxiety, or multiple sclerosis.

* * * * *